(12) United States Patent
Rodriguez et al.

(10) Patent No.: US 10,258,480 B1
(45) Date of Patent: Apr. 16, 2019

(54) SURGICALLY IMPLANTABLE JOINT SPACER

(71) Applicants: Carlos Andres Rodriguez, Punta Gorda, FL (US); Cira Rodriguez, Miami, FL (US)

(72) Inventors: Carlos Andres Rodriguez, Punta Gorda, FL (US); Cira Rodriguez, Miami, FL (US)

( * ) Notice: Subject to any disclaimer, the term of this patent is extended or adjusted under 35 U.S.C. 154(b) by 335 days.

(21) Appl. No.: 15/138,191

(22) Filed: Apr. 25, 2016

Related U.S. Application Data

(63) Continuation-in-part of application No. 13/943,333, filed on Jul. 16, 2013, now Pat. No. 9,320,611.

(60) Provisional application No. 61/716,534, filed on Oct. 20, 2012.

(51) Int. Cl.
*A61F 2/44* (2006.01)

(52) U.S. Cl.
CPC ............ *A61F 2/442* (2013.01); *A61F 2/4425* (2013.01); *A61F 2/4455* (2013.01); *A61F 2230/0076* (2013.01)

(58) Field of Classification Search
CPC ....... A61F 2/442; A61F 2/4425; A61F 2/4455
See application file for complete search history.

(56) References Cited

U.S. PATENT DOCUMENTS

| 5,059,193 A | 10/1991 | Kuslich |
| 5,171,278 A | 12/1992 | Pisharodi |
| 5,693,100 A | 12/1997 | Pisharodi |
| 5,800,526 A | 9/1998 | Anderson |
| 6,395,035 B2 | 5/2002 | Bresina |
| 6,595,998 B2 | 7/2003 | Johnson et al. |
| 7,070,598 B2 | 7/2006 | Um |
| 7,166,131 B2 | 1/2007 | Studer et al. |
| 7,238,186 B2 | 7/2007 | Zdeblick |
| 7,645,301 B2 | 1/2010 | Hudgins |
| 7,666,226 B2 | 2/2010 | Schaller |

(Continued)

FOREIGN PATENT DOCUMENTS

| EP | 1259179 | 11/2002 |
| EP | 1928332 | 6/2008 |

(Continued)

*Primary Examiner* — David W Bates
(74) *Attorney, Agent, or Firm* — Allen D Hertz, P.A.; Allen D. Hertz

(57) ABSTRACT

A spacer formed of an intermetallic compound, such as nitinol. The spacer includes at least two segments shaped in opposing arches. The unique properties of the intermetallic compound enable the material to be deformed into a planar, insertable shape when the material is cooled below a transition temperature and returns to the undeformed shape when the material returns to an ambient, operational temperature. An expansion mechanism assembly engages with the spacer to apply an expansion force, extending the spacer longitudinally drawing the spacer into the planar configuration. The expansion mechanism assembly can be used to guide the spacer into the desired position within the patient. The spacer control mechanism assembly is subsequently removed, relieving the expansion force, returning the spacer to the natural un-deformed, arched shape as it returns to body temperature. Retention features can be integrated in the spacer to aid in retaining the spacer in location.

21 Claims, 23 Drawing Sheets

(56) References Cited

U.S. PATENT DOCUMENTS

| | | |
|---|---|---|
| 7,758,647 B2 | 7/2010 | Arnin et al. |
| 7,857,857 B2 | 12/2010 | Kim |
| 7,955,384 B2 | 6/2011 | Rafiee |
| 7,959,652 B2 | 6/2011 | Zucherman |
| 8,097,018 B2 | 1/2012 | Malandain |
| 8,231,639 B2 | 7/2012 | Bolduc et al. |
| 8,231,678 B2 | 7/2012 | Lambrecht |
| 8,236,055 B2 | 8/2012 | Cordaro |
| 8,439,972 B2 | 5/2013 | Badawi |
| 8,529,628 B2 | 9/2013 | Marino |
| 8,778,027 B2 | 7/2014 | Medina |
| 9,320,611 B2 * | 4/2016 | Rodriguez .............. A61F 2/442 |
| 2006/0282166 A1 | 12/2006 | Molz et al. |
| 2006/0293753 A1 | 12/2006 | Thramann |
| 2008/0140203 A1 | 6/2008 | Davis |
| 2008/0281364 A1 | 11/2008 | Chirico et al. |
| 2009/0012564 A1 | 1/2009 | Chirico et al. |
| 2009/0118836 A1 | 5/2009 | Cordaro |
| 2009/0163918 A1 | 6/2009 | Levy |
| 2009/0204216 A1 | 8/2009 | Biedermann et al. |
| 2010/0063548 A1 | 3/2010 | Wang |
| 2010/0228289 A1 | 9/2010 | Park |
| 2011/0004308 A1 | 1/2011 | Marino et al. |
| 2011/0054538 A1 | 3/2011 | Zehavi et al. |
| 2011/0093075 A1 | 4/2011 | Duplesis et al. |
| 2011/0245926 A1 | 10/2011 | Kitchen |
| 2012/0116520 A1 | 5/2012 | Cauthen, III et al. |

FOREIGN PATENT DOCUMENTS

| | | |
|---|---|---|
| WO | WO 2005/097006 | 10/2005 |
| WO | WO 2007/002602 | 1/2007 |
| WO | WO 2007/117908 | 10/2007 |
| WO | WO 2008/022206 | 2/2008 |

* cited by examiner

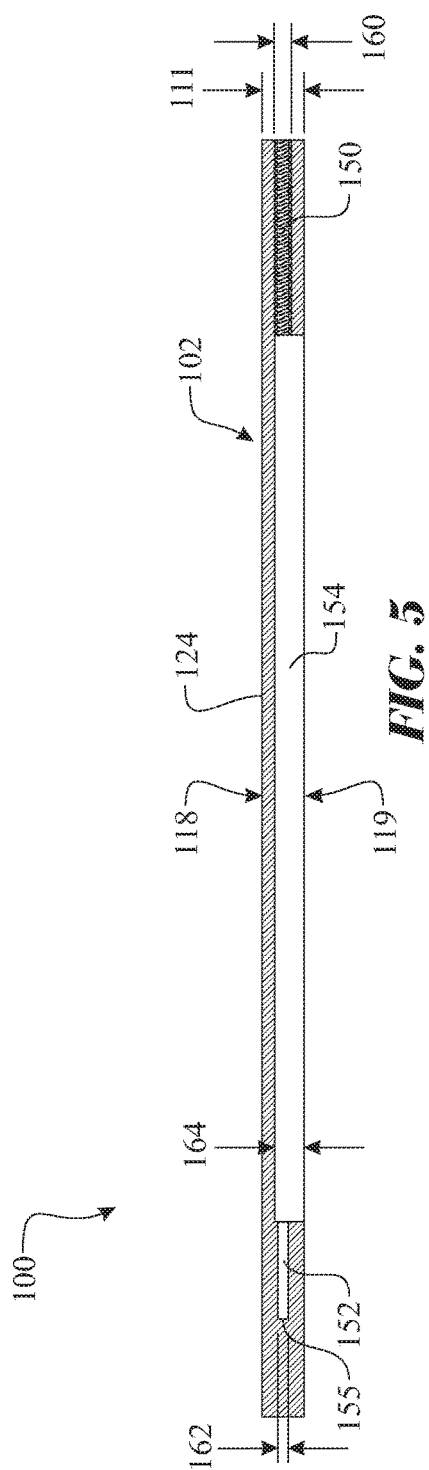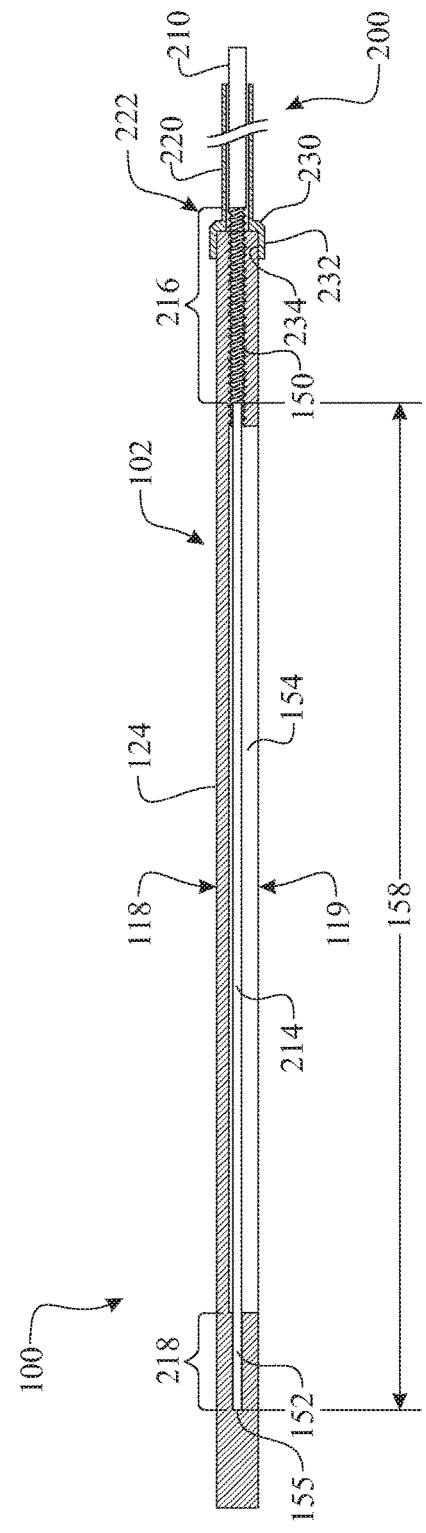

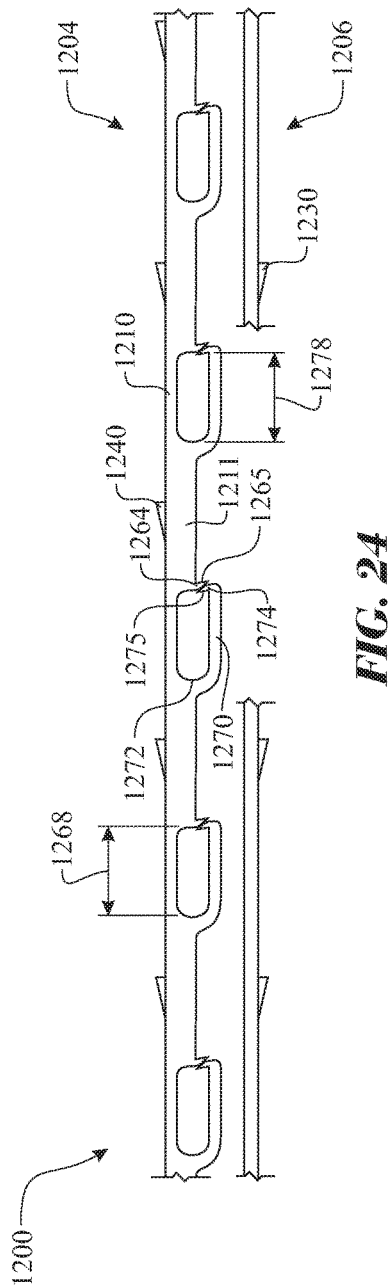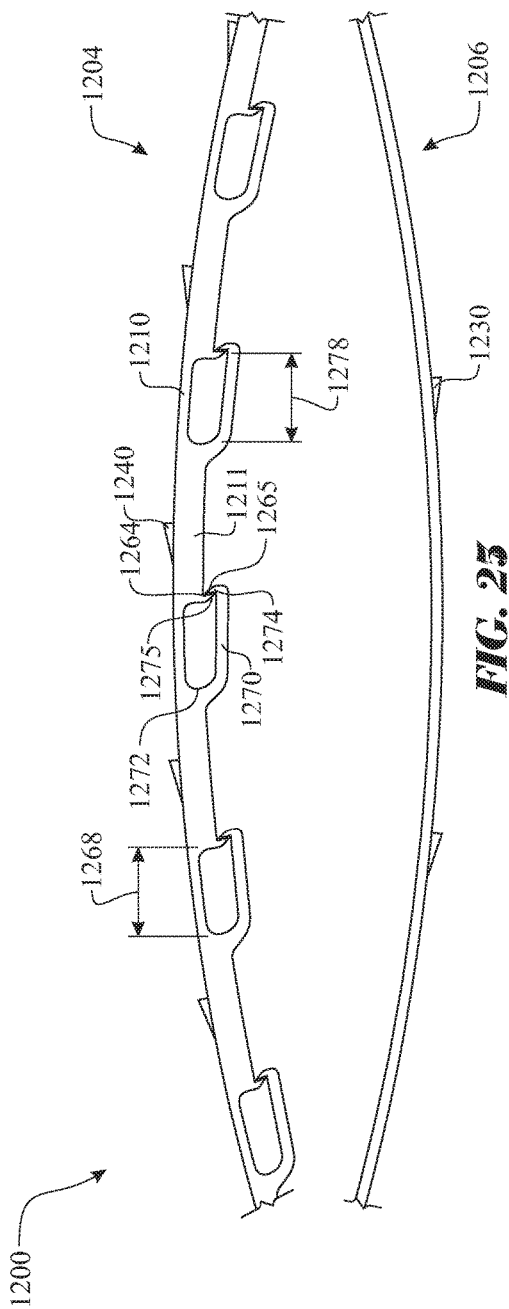

SURGICALLY IMPLANTABLE JOINT SPACER

CROSS-REFERENCE TO RELATED APPLICATIONS

This United States Non-Provisional Utility Application is a Continuation-In-Part, claiming the benefit of U.S. Provisional patent application Ser. No. 13/943,333, filed on Jul. 16, 2013 (scheduled to issue as U.S. Pat. No. 9,320,611 on Apr. 26, 2016), which claims the benefit of U.S. Provisional Patent Application Ser. No. 61/716,534, filed on Nov. 15, 2012, both of which are incorporated herein in their entireties.

FIELD OF THE INVENTION

The present disclosure generally relates to a medically implanted spacer. More particularly, the present disclosure relates to a medically implanted spacer for insertion within a joint formed between two adjacent bones to enhance movement or fuse in a deteriorated biological joint.

BACKGROUND OF THE INVENTION

Biological joints can degrade over time, deteriorate as a result of a birth defect or a disease, become damaged as a result of an accident or unwarranted motion, malformations due to incorrect growths, and the like. As the joint deviates from a normal, mobile condition, the malformed joint can cause multiple issues to the individual or animal, including sporadic or constant pain, limited motion, any degree of incapacitation, and the like.

Common joints that require surgical attention include inter-vertebrae discs, hips, knees, shoulders, elbows, and the like.

Inter-vertebrae discs can degrade over time or become damaged where they no longer function properly. The defective inter-vertebrae discs allow unwarranted motion between two adjacent vertebrae. The defective inter-vertebrae discs limit or reduce the support along the individual's spine. Over time, the defective inter-vertebrae disc needs surgical attention. Inter-vertebrae discs are addressed by fusing two or more adjacent vertebrae together. One short-term drawback of this procedure is the resulting limitation of motion incurred by the individual. A long-term drawback is that over time, the fused region increases stresses on adjacent joints, resulting in additional surgical procedures to fuse other regions of the individual's spine.

Other joints, such as hips and shoulders, are commonly formed having a first end of one bone moveably engaged with a mating end of a mating bone. Most joints comprise a first joint member formed in a ball and the mating joint member formed in a socket. As either or both of the surfaces of the joint members wears or deteriorates, the support of the joint degrades, hindering the mobility of the individual. In addition to the reduced mobility, the deteriorating joint can cause inflammation, discomfort, and other unwanted physical and psychological issues.

A few material compositions are known that have a unique property, a reversible, solid-state phase transformation known as a martensitic transformation. One of these material compositions is Nickel titanium, also known as nitinol. Nitinol is a metal alloy of nickel and titanium, where the two elements are present in roughly equal atomic percentages.

Nitinol alloys exhibit two closely related and unique properties: shape memory and superelasticity (also called pseudoelasticity). Shape memory refers to the ability of nitinol to undergo deformation at one temperature, and then recover its original, undeformed shape upon heating above its "transformation temperature". Superelasticity occurs at a narrow temperature range below its transformation temperature; in this case, no heating is necessary to cause the undeformed shape to recover, and the material exhibits enormous elasticity, some 10-30 times that of ordinary metal. The elasticity commonly occurs at a lower temperature, where the material recovers to its original shape upon returning to an ambient temperature.

Nitinol has an additional benefit, where the material is conducive to medical applications. The material can be surgically implanted into a patient with very limited risk of biological rejection.

Therefore, what is desired is a device capable of being surgically implanted to repair or overcome medial deficiencies of a damaged or defective biological joint.

SUMMARY OF THE INVENTION

The present disclosure is generally directed to a surgically implanted spacer for use in a joint formed between adjoining ends of two bones.

In a first aspect, the surgically implantable spacer may include:
  a spacer member formed of a material having martensitic properties;
  a pair of segment defining slots formed through the spacer member, each slot routed longitudinally, extending from a location proximate a first end of the spacer member to a location proximate a second end of the spacer member, each slot being located between a centerline and a respective edge of the spacer member;
  the pair of slots segmenting the spacer member into a circumferentially located, implanted spacer peripheral segment and a centrally located implanted spacer inner segment;
  a threaded shaping passage extending inward from the first spacer member end oriented along a spacer member longitudinal centerline;
  a blind receptacle in linear alignment with the threaded shaping passage initiating at a blind receptacle orifice and extending towards the second spacer member end;
  wherein the spacer member is shaped into an undeformed, operating temperature configuration having the implanted spacer peripheral segment forming an arch in a first direction and the implanted spacer inner segment forming an arch in a first direction, wherein the first direction is opposite of the second direction.

In a second aspect, the arches of the surgically implantable spacer are straightened with an insertion of a spacer shaping control rod, wherein a threaded segment of the spacer control rod engages with the threaded shaping passage and an extension segment of the spacer control rod engages with a distal end of the blind receptacle.

In another aspect, the straightening process is enhanced by reducing the temperature of the spacer member to a temperature that is below a transformation temperature.

In yet another aspect, the spacer shaping control rod is inserted through a spacer control sleeve.

In yet another aspect, a spacer torsional control element is affixed to the spacer control sleeve. The spacer torsional control element comprises at least one spacer torsional control section having a spacer torsional control surface, wherein the spacer torsional control surface engages with a surface of the spacer member.

In yet another aspect, the spacer torsional control element comprises a pair of spacer torsional control sections, each section having a spacer torsional control surface, wherein the spacer torsional control surface engages with a respective surface of the spacer member.

In yet another aspect, an interior surface of the blind receptacle is smooth.

In yet another aspect, the spacer member further comprises a spacer control rod clearance slot formed in one side thereof, the spacer control rod clearance slot spanning between the threaded shaping passage and the blind receptacle.

In yet another aspect, the spacer member is shaped in an oblong oval shape.

In yet another aspect, each segment defining slot is shaped having an arch, the arch having a radial center located on side of the longitudinal axis that is opposite of the slot.

In yet another aspect, the spacer member further comprises a slot stress relief formed at each end of the segment-defining slot. The slot stress relief is preferably formed as a circular hole.

In yet another aspect, the spacer member further comprises at least one retention feature. The retention feature can be a tab that is cut, shaped and formed from the material of the spacer member.

In yet another aspect, the spacer member further comprises a series of retention features located along the circumferential outer edge.

In yet another aspect, the spacer member further comprises a series of retention features located along the circumferential inner edge.

In yet another aspect, the spacer member further comprises a series of retention features located along the circumferential edge of the inner segment.

In yet another aspect, the retention features are oriented extending outward when the spacer member is placed into an undeformed, operating temperature configuration.

In yet another aspect, the spacer shaping control rod is inserted through a spacer control sleeve.

In yet another aspect, the surgically implantable spacer is inserted between two adjacent vertebrae.

In yet another aspect, the surgically implantable spacer is inserted within one of: a hip joint, a shoulder joint, a knee, an elbow, and the like.

In yet another aspect, the spacer member is fabricated of a planar sheet of material.

In yet another aspect, the spacer member is fabricated of a planar sheet of material having a thickness providing suitable rigidity for the target application.

In yet another aspect, the operational segment of the spacer expansion control assembly has a diameter suitable for the application. In one exemplary embodiment, the diameter of the segment is smaller than the thickness of the spacer member.

In yet another aspect, the spacer member is fabricated of a planar sheet of material having a thickness up to 12 mm, with a preferred thickness of up to 9 mm.

In yet another aspect, the spacer member is fabricated of a planar sheet of material having a thickness of between 3 mm and 12 mm, with a preferred thickness of between 3 mm and 9 mm.

In yet another aspect, the spacer member is fabricated of a planar sheet of material having a thickness of between 5 mm and 12 mm, with a preferred thickness of between 5 mm and 9 mm.

In yet another aspect, the threaded shaping passage has a diameter of approximately 3 mm.

In yet another aspect, the blind receptacle has a diameter of approximately 2 mm.

In yet another aspect, the spacer control rod clearance slot extends inward from a bottom surface of the spacer member. The spacer control rod clearance slot would have a depth suitable to accommodate the operational segment of the spacer expansion control assembly. For example, where the operational segment of the spacer expansion control assembly has a diameter of 3 mm, the spacer control rod clearance slot would have a depth of approximately 5 mm.

In yet another aspect, a spacer insertion end of the spacer member is shaped to provide a circumferential edge that broadens as it extends from the spacer insertion end. The shape of the spacer insertion end provides a lead in to aid in an insertion process.

In yet another aspect, the spacer member is fabricated of a material considered to have a more complicated monoclinic crystal structure known as martensite at lower temperatures.

In yet another aspect, the spacer member is fabricated of nitinol.

In yet another aspect, the present invention discloses a method of use, the method comprising steps of:
  obtaining a surgically implantable spacer;
  reducing a temperature of the surgically implantable spacer to a temperature below the transformation temperature wherein the material becomes super-elastic;
  extending the surgically implantable spacer into a planar shape by applying an extending force to the surgically implantable spacer;
  inserting the surgically implantable spacer into a biological joint;
  removing the extending force from the surgically implantable spacer; and
  warming the spacer to a temperature above the transformation temperature, wherein the material returns to its undeformed shape.

In yet another aspect, the process further comprises a step of retaining the surgically implantable spacer in position by including at least one retention feature.

In yet another aspect, the process continues by grafting material through any of a series of features of the surgically implantable spacer.

In yet another aspect, the surgically implantable spacer can be used in non-joint medical applications wherein the spacer is implanted in an application where the change in shape due to the nature of the material provides an advantage. Examples include aiding in healing a fracture, reshaping a curved region, where the insertion is linear (such as a nasal implant), and the like.

In yet another aspect, the surgically implantable spacer can include three separate spacer elements pivotally assembled to one another using an assembly pin.

In yet another aspect, the surgically implantable spacer can include three separate spacer elements pivotally assembled to one another using an assembly pin. The assembly pins can be configured to retain a clearance for the spacer shaping control rod of the spacer expansion control mechanism assembly.

In yet another aspect, the surgically implantable spacer can include three separate spacer elements pivotally assembled to one another using an assembly pin, wherein the assembly pin is located proximate each distal end of the spacer elements.

In yet another aspect, the surgically implantable spacer can include three separate spacer elements pivotally assembled to one another using an assembly pin, wherein the assembly pin is located inward from each distal end of the spacer eleme0nts.

In yet another aspect, the threaded shaping passage can be formed within a pivotal threaded expansion shaping element pivotally assembled to the three separate spacer elements forming the surgically implantable spacer. The pivotal threaded expansion shaping element would include a pair of pivotal axles or pins extending radially and linearly outward from the pivotal threaded expansion shaping element, retaining a threaded passageway extending therethrough.

In yet another aspect, the blind receptacle can be formed within a pivotal blind receptacle expansion shaping element pivotally assembled to the three separate spacer elements forming the surgically implantable spacer. The pivotal blind receptacle expansion shaping element would include a pivotal axle or pin extending radially through the pivotal blind receptacle expansion shaping element at a location to avoid interfering with the blind receptacle formed therein.

In yet another aspect, the three separate spacer elements can include pin receiving cavities or bores to receive the respective pins. In one variant, the spacer central segment can include slots, replacing the pin receiving cavities or bores to improve assembly of the surgically implantable spacer. The slots are preferably formed parallel to a tangent direction of a radius from an opposing pivotal pin or axle. It is preferred that the slots be formed in the end of the spacer central segment receiving the pivotal threaded expansion shaping element.

In yet another aspect, the surgically implantable spacer can include a series of bores, wherein each of the bores is oriented substantially perpendicular to an elongated axis of the body of the surgically implantable spacer and arranged extending through a generally centered area thereof. The spacer would be retained in a compact, planar configuration by compressing the centers of the spacer segments to one another and inserting a spacer compression retention control rod of a spacer compression retention mechanism assembly therethrough. The spacer compression retention control rod would retain the three segments in a generally planar configuration prior to and during insertion. This enables insertion from an anterior (front) side of the vertebra.

In yet another aspect, the surgically implantable spacer can employ a spacer retention component to maintain separation between the spacer elements.

In yet another aspect, the spacer retention component is a threaded element, comprising threading on an exterior surface.

In yet another aspect, the spacer retention component is an insertable planar spacing retention component. The insertable planar spacing retention component can include locating and retention features.

In yet another aspect, the locating features can include slots extending inward from opposing sides of the segments of the surgically implantable spacer; an axis of the slots extending substantially perpendicular to an elongated axis of the body of the surgically implantable spacer and located along a generally centered area thereof.

In yet another aspect, the retention features can include a plurality of notches, having a portion of the notches formed as a rabbet located at each respective corner of the insertable planar spacing retention component and another portion of the notches formed as a groove across a central portion of a respective edge. The outward extending walls of each notch ensure the insertable planar spacing retention component remains in position throughout the lifespan of the surgically implantable spacer.

In yet another aspect, the spacer retention component is a pivotal spanner component. The pivotal spanner component is pivotally assembled between the pair of spacer peripheral segments.

In yet another aspect, the pivotal spanner component can include a narrowed distal edge adapted to engage with a slot or groove formed in the respective mating surface of the spacer central segment. The spacer central segment can include a series of slots or grooves to receive the narrowed distal edge of the pivotal spanner component, enabling the pivotal spanner component to support any suitable separation distance between the spacer central and peripheral segments.

In yet another aspect, the narrowed distal edge can be formed having a tapered edge, wherein the tapered edge is shaped to aid in the rotational positioning process of the pivotal spanner component.

In yet another aspect, the spacer retention component can additionally include at least one grafting cavity.

In yet another aspect, the grafting cavity can be formed as a bore extending into a body of the spacer retention component.

In yet another aspect, the grafting cavity can be formed as an aperture extending through the body of the spacer retention component.

In yet another aspect, the surgically implantable spacer can include at least one bendable segment. The bendable segment includes a planar exterior, convex forming surface and at least one cantilevered hook for engagement with a mating latching feature formed on an interior, concave forming surface. The mating latching feature can be provided as an opposingly oriented, mating cantilevered hook, a mating hook, a notch or slot, a series of notches or slots, and the like. In operation, as two opposite ends of the bendable segment are drawn towards one another, the at least one cantilevered hook engages with the mating latching feature to retain the bendable segment in an arched shape.

In yet another aspect, the arrangement of at least one cantilevered hook includes at least two cantilevered hooks, wherein the at least two cantilevered hooks defines a recessed formation between each pair of adjacent cantilevered hooks.

In yet another aspect, the surgically implantable spacer includes a pair of bendable segments, each bendable segment comprising a plurality of cantilevered hook latching configurations. Each bendable segment is designated having a cantilevered hook end and a mating latching feature end. A pair of like bendable segments are hingeably joined to one another using any suitable design at each of two distal ends. The bendable segments are arranged having each cantilevered hook latching side facing one another and oriented having the cantilevered hook end of a first bendable segment in registration with the mating latching feature end of the second bendable segment. The planar surface of each of the pair of bendable segments would be oriented defining an exterior surface of the assembly.

In yet another aspect, the surgically implantable spacer includes one bendable segment and a planar segment, the bendable segment comprising a plurality of cantilevered hook latching configurations and the planar segment having two substantially planar surfaces. The bendable segment and the planar segment are hingeably joined to one another using any suitable design at each of two distal ends. The planar segment is located facing the cantilevered hook latching side of the latching bendable segment. In one configuration, the bendable segment and the planar segment are adapted to bend in opposite directions at approximately similar arches. In a second configuration, the bendable segment is adapted to bend and the planar segment is adapted to remain substantially planar. This would require an inclusion of a moveable hinged configuration in at least one end of the surgically implantable spacer.

In yet another aspect, the cantilevered hook latching configurations are spatially arranged defining a spacer frame segment.

In yet another aspect, a plurality of spatially arranged grafting retention features are formed along and exterior surface of the spacer frame segment.

In yet another aspect, a plurality of spatially arranged grafting retention features are formed along and exterior surface of the planar segment.

These and other aspects, features, and advantages of the present invention will become more readily apparent from the attached drawings and the detailed description of the preferred embodiments, which follow.

BRIEF DESCRIPTION OF THE DRAWINGS

The invention will now be described, by way of example, with reference to the accompanying drawings, in which:

FIG. 5 presents a sectioned elevation view of the surgically implantable spacer, the section being taken along section line 5-5 of FIG. 1;

FIG. 6 presents a sectioned elevation view of the surgically implantable spacer, the section being taken along section line 5-5 of FIG. 1, the illustration further comprising the spacer control mechanism assembly to show the interaction therebetween;

FIG. 24 presents a side elevation partial view of another exemplary surgically implantable spacer, the surgically implantable spacer comprising a pair of self locking surgically implantable spacer segments, wherein the self locking feature includes a plurality of cantilevers hooks and mating rigid hooks, the illustration presenting the surgically implantable spacer in a pre-insertion, collapsed, planar configuration;

FIG. 25 presents a side elevation partial view of the exemplary surgically implantable spacer originally introduced in FIG. 24, the illustration presenting the surgically implantable spacer in an inserted, expanded configuration;

Like reference numerals refer to like parts throughout the several views of the drawings.

DETAILED DESCRIPTION OF THE INVENTION

Figure 1:
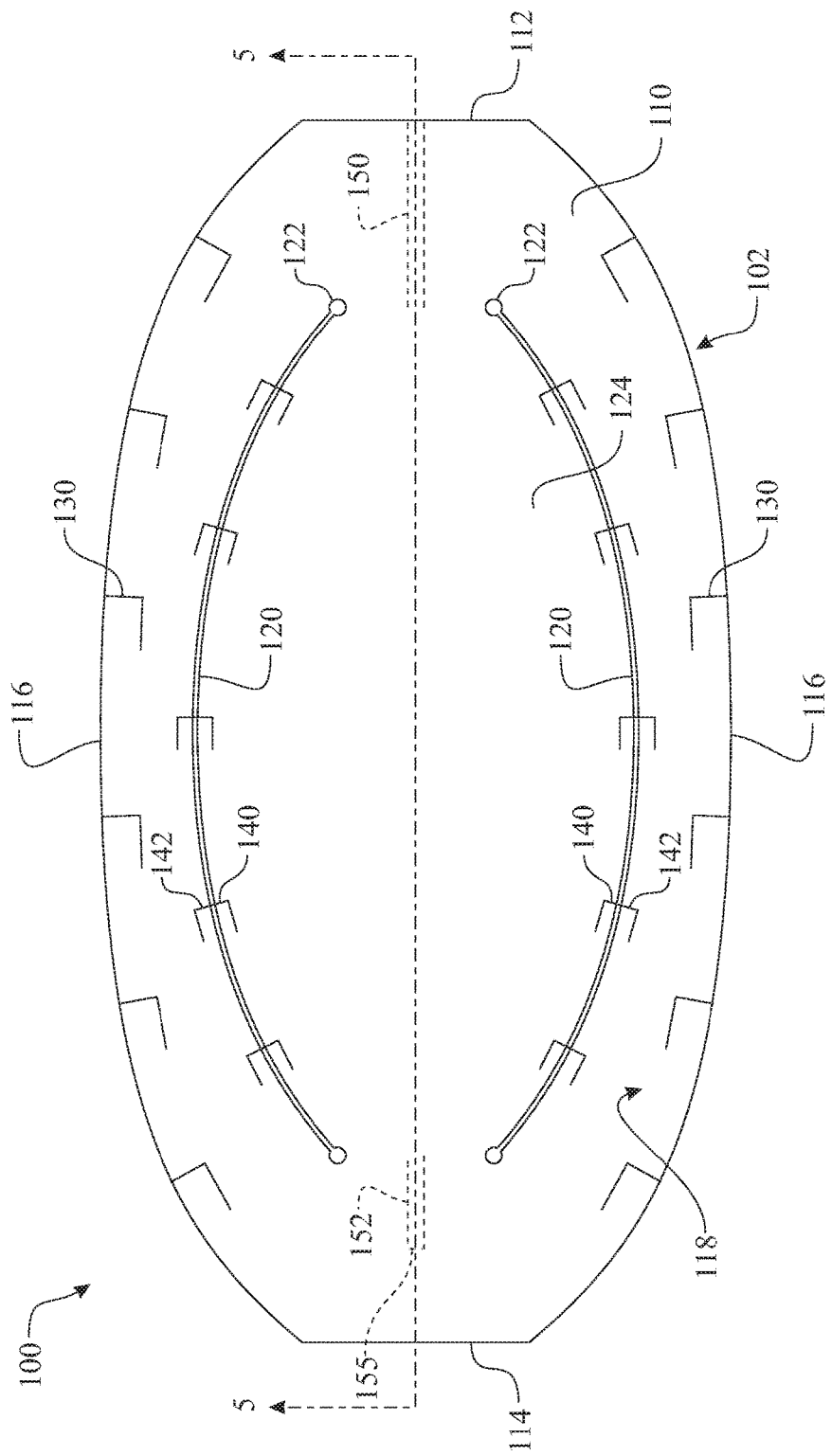
FIG. 1 presents a top view of an exemplary surgically implantable spacer, the surgically implantable spacer being shown in a super-elastic state and in a planar configuration.
Figure 2:
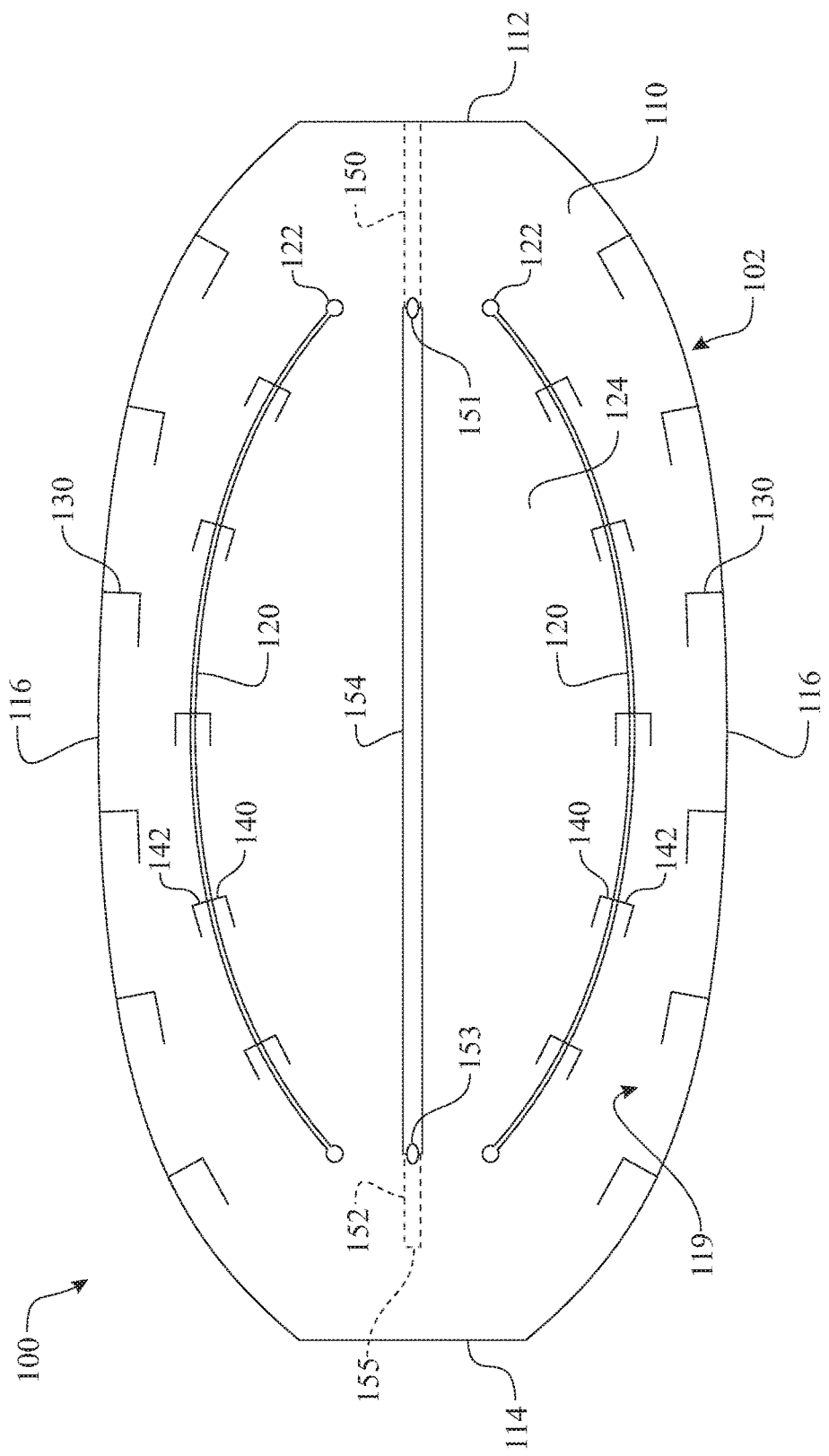
FIG. 2 presents a bottom view of the surgically implantable spacer originally introduced in FIG. 1.
Figure 3:
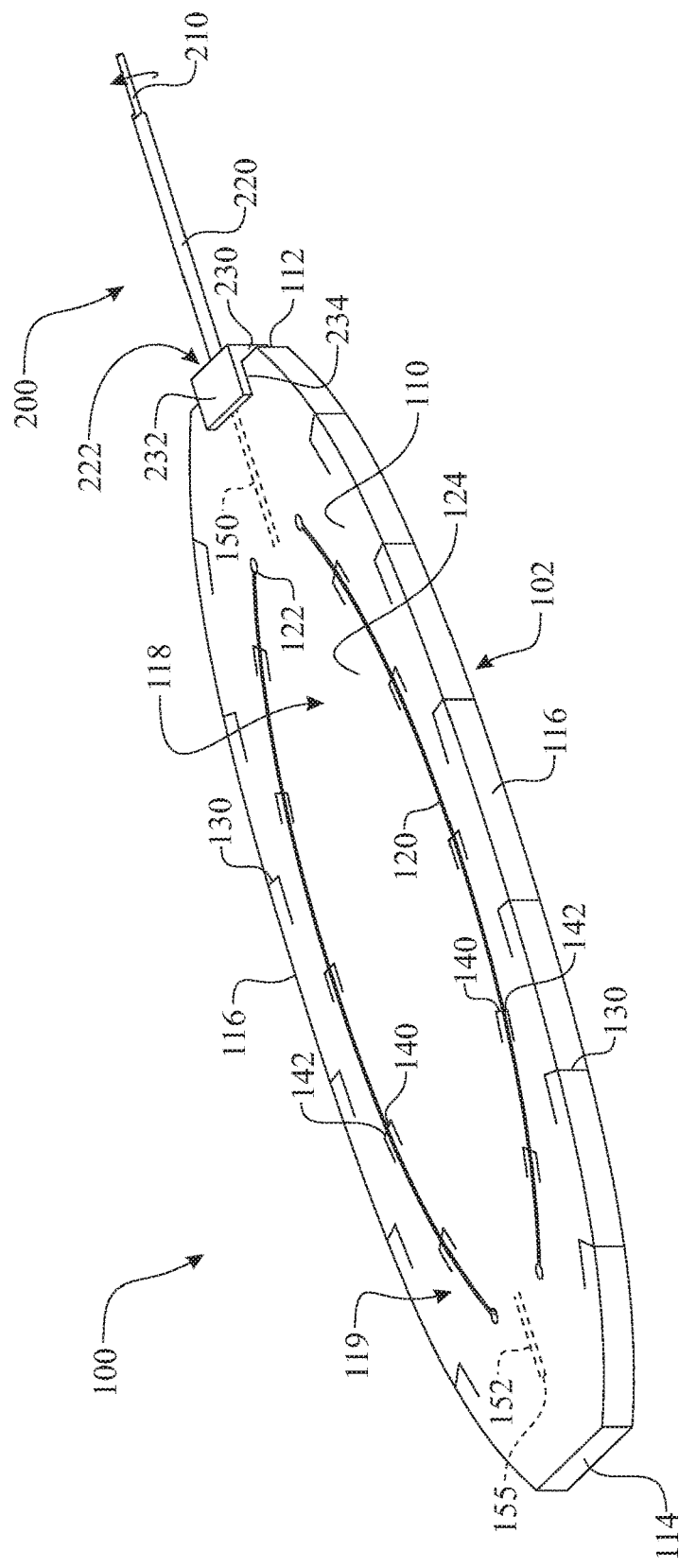
FIG. 3 presents an isometric top view of the surgically implantable spacer originally introduced in FIG. 1, the illustration introduces a spacer control mechanism assembly.
Figure 4:
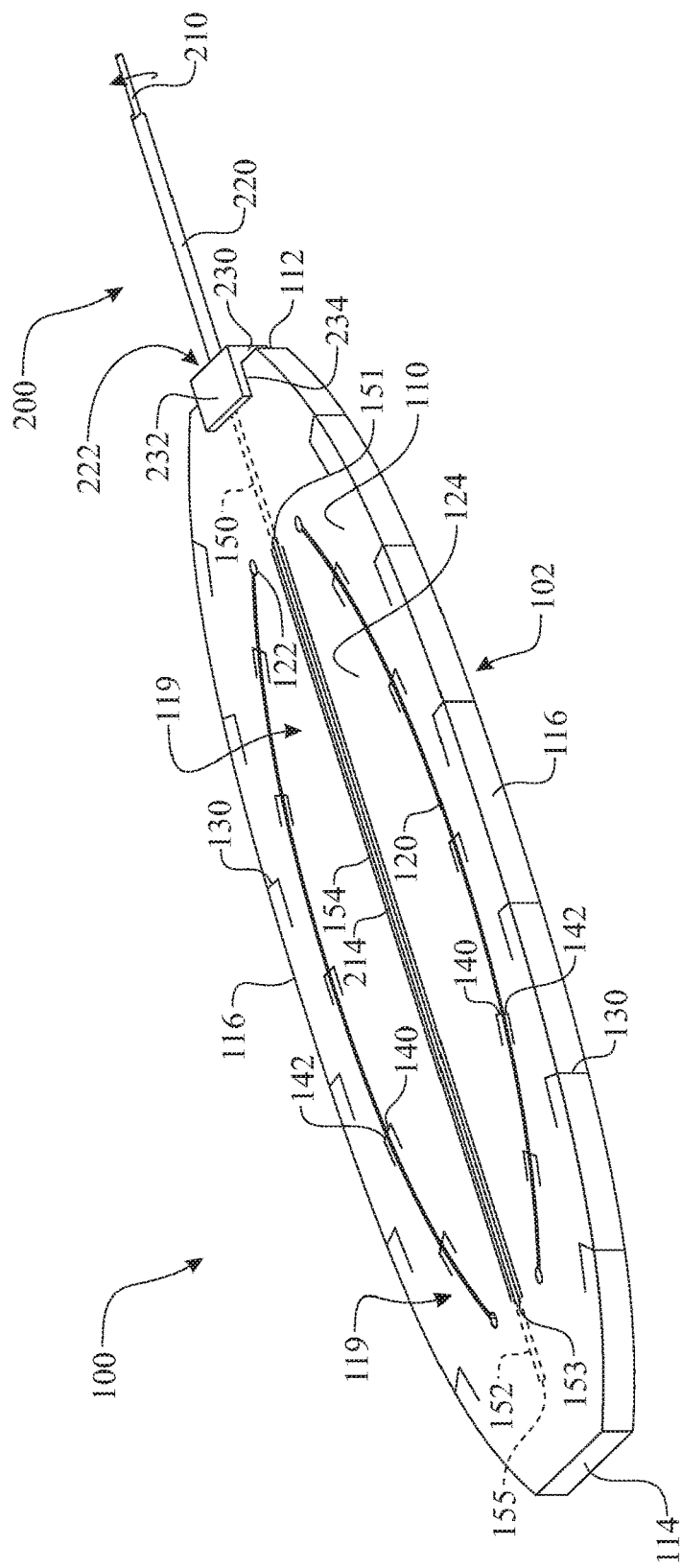
FIG. 4 presents an isometric bottom view of the surgically implantable spacer in a configuration as previously shown in FIG. 3.
Figure 7:
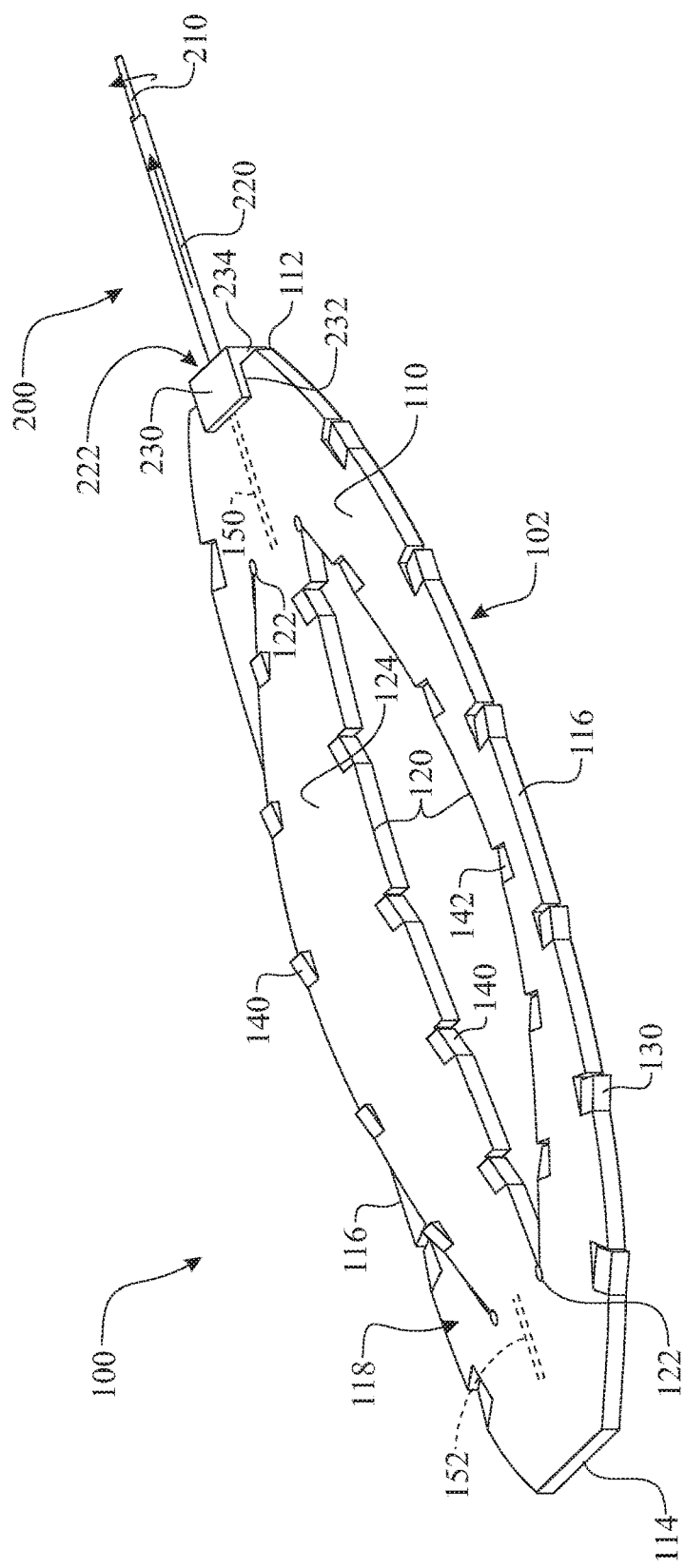
FIG. 7 presents an isometric top view of the surgically implantable spacer, the surgically implantable spacer being shown removing a shaping force and returning to an undeformed shape.
Figure 8:
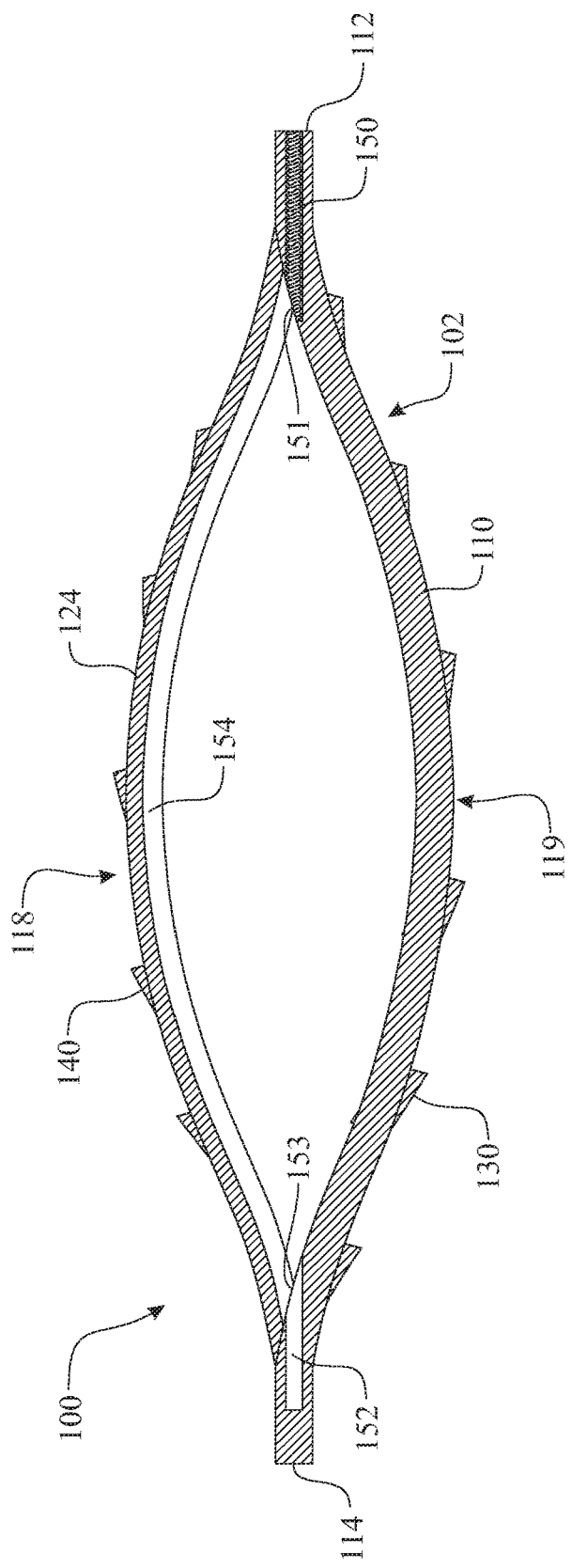
FIG. 8 presents an sectioned elevation view of the surgically implantable spacer, the surgically implantable spacer being shown in the undeformed shape.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

The present disclosure is generally directed to a surgically implantable spacer 100 as illustrated in FIGS. 1 through 8. In some applications, the surgically implantable spacer 100 can be more specifically referred to as a surgically implantable disc 100. It is noted that the thickness and at least a portion of the features and shapes presented in the figures are exaggerated for clarity. The surgically implantable spacer 100 is preferably shaped from a planar sheet of raw material. The material can be any biologically acceptable material, preferably of one that has a unique property, which is a reversible, solid-state phase transformation known as a martensitic transformation. The surgically implantable spacer 100 can be provided in any suitable shape, with the preferred shape being illustrated in the respective figures and described herein. The surgically implantable spacer 100 is shaped having a peripheral edge comprising a planar spacer control end 112, a spacer insertion end 114, and a pair of spacer side edges 116. Each spacer side edge 116 spans between similar ends of the planar spacer control end 112 and spacer insertion end 114. Each side spanning between the spacer control end 112 and the spacer insertion end 114 is preferably arched outward from a center thereof. The orientation of the spacer body 102 can be referenced by the spacer control end 112, the spacer insertion end 114, a spacer upper surface 118 defining a first side thereof, and a spacer lower surface 119 defining a second, opposite side thereof.

The surgically implantable spacer 100 is segmented into an implanted spacer peripheral segment 110 and an implanted spacer inner segment 124 by a pair of segment defining slots 120. Each segment defining slot 120 is formed cutting through the spacer body 102. The segment defining slot 120 can be formed using a Wire Electric Discharge Machining (WEDM) process. It is understood that alternative cutting methods can be employed to form the segment defining slots 120. Each segment defining slot 120 spans along a longitudinal length of the spacer body 102, spanning between a location proximate the spacer control end 112 and a location proximate the spacer insertion end 114. Each segment defining slot 120 would be located between a longitudinal centerline and a peripheral edge of the spacer body 102 segmenting the spacer body 102 into the implanted spacer peripheral segment 110 and the implanted spacer inner segment 124. An optional slot stress relief 122 can be formed at each end of the segment defining slot 120 to increase the long-term reliability of the surgically implantable spacer 100. The segment defining slots 120 can be formed in any suitable shape, including linear, rectangular, arched, freeform, and the like.

A spacer control mechanism assembly receiving interface is formed in the spacer body 102. The spacer control mechanism assembly receiving interface comprises a threaded shaping passage 150, a blind receptacle 152 and a spacer control rod clearance slot 154 spanning therebetween. Each of the elements of the spacer control mechanism assembly receiving interface 150, 152, 154 are preferably provided in a linear arrangement with one another. The preferred embodiment locates the spacer control mechanism assembly receiving interface 150, 152, 154 along a longitudinal centerline of the spacer body 102. The threaded shaping passage 150 extends inward from the spacer control end 112, terminating at a threaded shaping aperture orifice 151. The blind receptacle 152 initiates at a blind receptacle orifice 153 located at a transition between the implanted spacer peripheral segment 110 and the implanted spacer inner segment 124 in a region proximate the spacer insertion end 114 and extends outward towards the spacer insertion end 114, terminating at a receptacle end wall 155. The receptacle end wall 155 is located prior to the spacer insertion end 114.

A spacer expansion control mechanism assembly 200 is provided to engage with the spacer body 102, and more specifically, the spacer control mechanism assembly receiving interface. The spacer expansion control mechanism assembly 200 comprises a spacer shaping control rod 210 extending through a spacer control sleeve 220. The spacer shaping control rod 210 is segmented into a handle portion, a spacer control rod threaded segment 216, a spacer control rod spanning segment 214, and a spacer control rod extension segment 218. The handle portion extends from a gripping end to the spacer control rod threaded segment 216. The spacer control rod threaded segment 216 is threaded to threadably engage with the threaded shaping passage 150. A spacer control rod spanning segment 214 extends from the opposite end of the spacer control rod threaded segment 216 towards an expansion end. A spacer control rod extension segment 218 is defined as a portion of the spacer shaping control rod 210 located proximate the expansion end, wherein the spacer control rod extension segment 218 is designed to be inserted into and engage with the blind receptacle 152. A spacer torsional control element 230 is affixed to an engaging end 222 of the spacer control sleeve 220. The spacer torsional control element 230 can be provided in any shape to engage with the spacer body 102. The exemplary embodiment of the spacer torsional control element 230 illustrated in the figures includes a pair of spacer torsional control sections 232, each spacer torsional control section 232 having a spacer torsional control surface 234. The spacer torsional control surface 234 engages with the exterior surfaces 118, 119 of the spacer body 102 in a manner to apply a retention torque against the rotational force generated by threading the spacer control rod threaded segment 216 into the threaded shaping passage 150. The torque can be controlled during both insertion and removal of the spacer expansion control mechanism assembly 200. Although the exemplary embodiment of the spacer torsional control element 230 includes a pair of spacer torsional control sections 232, it is understood that the spacer torsional control element 230 can be designed in any shape suitable for the application.

The spacer expansion control mechanism assembly 200 would engage with the spacer body 102 by inserting the spacer control rod extension segment 218 of the spacer shaping control rod 210 through the threaded shaping passage 150, exiting the threaded shaping aperture orifice 151, continuing within the spacer control rod clearance slot 154, passing through the blind receptacle orifice 153 and seating the spacer control rod extension segment 218 into the blind receptacle 152. As the spacer control rod extension segment 218 approaches the blind receptacle 152, the spacer control rod threaded segment 216 would engage with the threaded shaping passage 150. Upon engagement, the spacer shaping control rod 210 would be rotated to threadably engage into the threaded shaping passage 150. This threaded engagement is employed to generate an expansion force 158. The expansion force 158 extends the spacer body 102 into a planar configuration. A first end of the expansion force 158 is applied at the interface between the spacer control rod threaded segment 216 and threaded shaping passage 150. A second end of the expansion force 158 is applied at the interface between the spacer control rod extension segment 218 and blind receptacle 152.

An optional series of retention features can be integrated into the spacer body 102. The exemplary embodiment presents a variety of retention features along several edges. A first exemplary retention feature is referred to as a circumferential outer edge retention feature 130. Each of the circumferential outer edge retention features 130 extends inward from the peripheral edge of the spacer body 102. Each circumferential outer edge retention feature 130 is shaped and oriented to allow insertion of the surgically implantable spacer 100 into the joint, while restraining against a reversed movement. A second exemplary retention feature is referred to as an inner segment retention feature 140. Each of the inner segment retention features 140 extends inward from the segment defining slot 120, extending into the implanted spacer inner segment 124. Like the circumferential outer edge retention feature 130, each inner segment retention feature 140 is also shaped and oriented to allow insertion of the surgically implantable spacer 100 into the joint, while restraining against a reversed movement. A third exemplary retention feature is referred to as a circumferential inner edge retention feature 142. Each of the circumferential inner edge retention features 142 extends outward from the segment defining slot 120, extending into the implanted spacer peripheral segment 110. Like retention features 130, 140, each circumferential inner edge retention feature 142 is also shaped and oriented to allow insertion of the surgically implantable spacer 100 into the joint, while restraining against a reversed movement. In the exemplary embodiment, the retention features 130, 140, 142 are spatially arranged along each respective edge. The retention features 130, 140, 142 are preferably designed to become planar when the spacer body 102 is placed into the planar configuration and return to an angled, retention configuration when the spacer body 102 is warmed and thus returns to the undeformed configuration. Although the exemplary embodiments presented in the figures are rectangular, it is understood that the retention features 130, 140, 142 can be shaped in any suitable shape, including square, triangular, elliptical, circular, hexagonal, trapezoidal, star shaped, and the like. Although not illustration, it is also understood that the spacer body 102 can be perforated.

The spacer body 102 can be fabricated of a planar sheet of suitable material. One exemplary suitable material would be nickel titanium, also known as nitinol or any other material known to be an intermetallic compound. The composition of the alloy would be such where the transformation temperature is below a patient's common lowest temperature at the subject joint. The spacer body 102 can be shaped using any suitable metal working process known by those skilled in the art, including Wire Electric Discharge Machining (WEDM), stamping, laser cutting, machining, chemical etching, and the like. The spacer body 102 can be finished using any suitable metal finishing process known by those skilled in the art, including sanding, grinding, polishing, electro-polishing, plating, rolling, and the like to remove any imperfections created during the fabrication process. The spacer body 102 would be formed into the desired undeformed configuration using commonly known processes for forming nickel titanium or similar suitable material having a shape-memory effect. Another exemplary metal would be a gold-cadmium alloy. This classification of material is known to have a more complicated monoclinic crystal structure known as martensite at lower temperatures.

The spacer control mechanism assembly receiving interface can be formed using a drilling process. The threaded shaping passage 150 and blind receptacle 152 are formed by drilling longitudinally into the spacer body 102 from the spacer control end 112. The drilling process stops when the end of the drill bit reaches the blind receptacle end wall 155. The threaded shaping passage 150 is subsequently threaded using any commonly known tapping process. The drilling process can be used to at least partially form the spacer control rod clearance slot 154.

The features would be cut using any suitable cutting process. This can include Wire Electric Discharge Machining (WEDM), stamping, laser cutting, machining, and the like. The features can include the segment defining slots 120, the slot stress relieves 122, and the retention features 130, 140, 142, and the like. The spacer control rod clearance slot 154 can be formed by any suitable process, including laser cutting, chemical etching, machining, and the like.

The spacer body 102 can be fabricated of the following dimensions: a spacer thickness 111 can be up to 12 mm, with a preferred thickness of up to 9 mm. It is understood that the spacer thickness can be between 3 mm and 12 mm, with a preferred thickness of between 3 mm and 9 mm. The threaded shaping passage 150 can be formed having a threaded passage diameter 160 of approximately 3 mm. The threaded passage diameter 160 would be sized respective to the diameter of the spacer control rod threaded segment 216.

The blind receptacle 152 can be formed having a smooth passage diameter 162 of approximately 2-2.75 mm and would also be sized respective to the diameter of the spacer control rod extension segment 218. The spacer control rod clearance slot 154 would have a depth suitable to accommodate the spacer control rod spanning segment 214 of the spacer shaping control rod 210. For example, where the spacer control rod spanning segment 214 of the spacer shaping control rod 210 has a diameter of 3 mm, the spacer control rod clearance slot 164 would have a depth of approximately 5 mm. The threaded passage diameter 160 would increase in diameter as a result of the tapping process.

Figure 10:
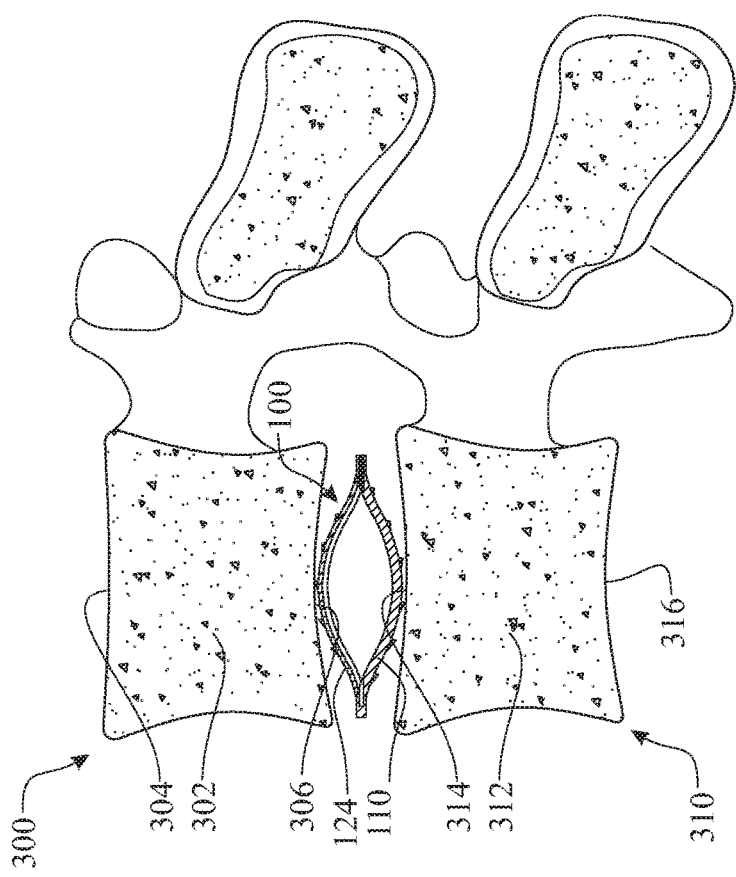
FIG. 10 presents an sectioned elevation view of the surgically implantable spacer shown in the exemplary biological application, wherein the surgically implantable spacer is shown inserted between two adjacent vertebrae.
Figure 11:
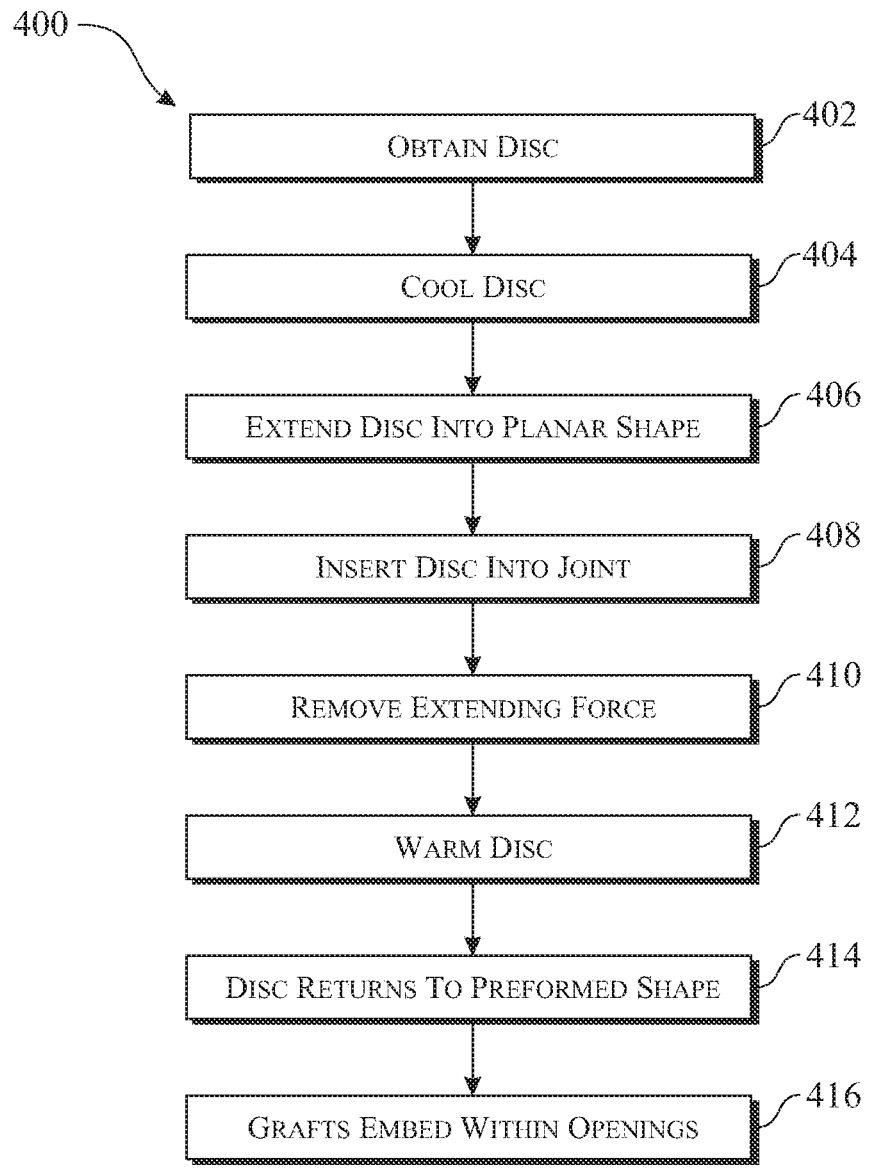
FIG. 11 presents an exemplary flow diagram describing a method of using the surgically implantable spacer.

In use, the surgically implantable spacer 100 optimizes the properties of the material. An exemplary application is presented in FIGS. 9 and 10, with FIG. 11 presenting a replacement spacer insertion process flow diagram 400 detailing the process. A first step of the replacement spacer insertion process flow diagram 400 would be to obtain a surgically implantable spacer 100 designed for the specific application (block 402). In a broadest representation, the surgically implantable spacer 100 is inserted within a joint formed between a first joint member 300 and a second joint member 310. The first joint member 300 and second joint member 310 are representative of any suitable joint.

Figure 9:
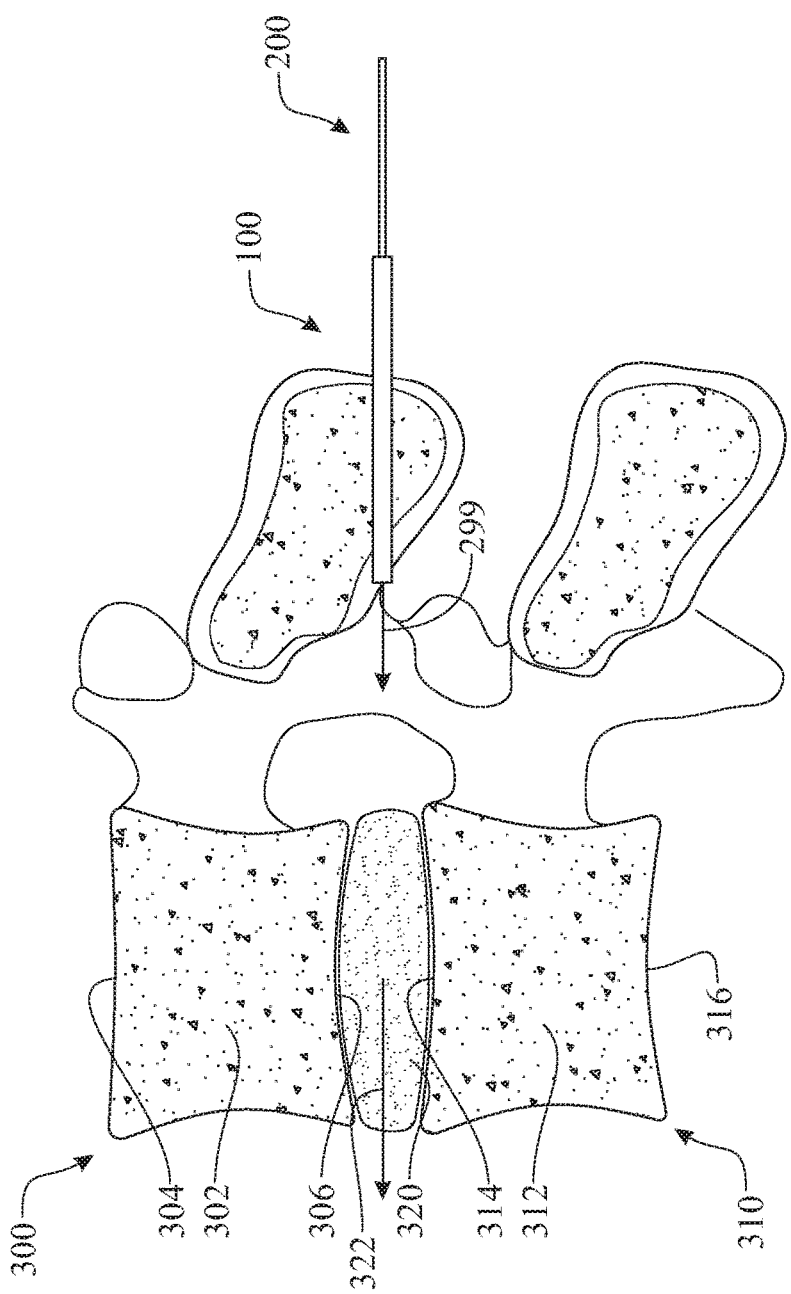
FIG. 9 presents an sectioned elevation view of the surgically implantable spacer shown in an exemplary biological application, wherein the surgically implantable spacer is shown being inserted between two adjacent vertebrae.

In the exemplary embodiment, the surgically implantable spacer 100 is designed to replace an inter-vertebrae disc 320. The intra-vertebral disc 320 would be located between two adjacent vertebrae 302, 312. Each vertebrae 302, 312 has a vertebrae first joint surface 304, 314 and a vertebrae second joint surface 306, 316. The joint surfaces can also be referred to as an end plate. The vertebrae first joint surface 314 is located adjacent to the vertebrae second joint surface 306. The intra-vertebral disc 320 is located between the vertebrae second joint surface 306 of the first vertebrae 302 and the vertebrae first joint surface 314 of the second vertebrae 312. During the insertion procedure, the intra-vertebral disc 320 is removed in accordance with an intra-vertebral disc removal 322 as illustrated in FIG. 9. Once the surgical site is readied, the surgically implantable spacer 100 is prepared for insertion (blocks 404, 406). The spacer body 102 is cooled to a temperature slightly below the transformation temperature (one suggested temperature would be below 70 degrees F.), wherein the material changes from a shape memory state to a super-elastic state (block 404). The spacer expansion control mechanism assembly 200 is assembled to the spacer control mechanism assembly receiving interface. As the spacer expansion control mechanism assembly 200 threadably engages with the threaded shaping passage 150, the spacer control rod extension segment 218 enters the blind receptacle 152. The distal end of the spacer control rod extension segment 218 eventually contacts the blind receptacle end wall 155. As the spacer expansion control mechanism assembly 200 continues to be threaded through the threaded shaping passage 150, an expansion force 158 is generated between the threaded shaping passage 150 and the blind receptacle end wall 155. The expansion force 158 extends the spacer body 102 into a planar configuration (block 406). The spacer torsional control element 230 engages with the spacer body 102 to counter any torsional forces generated by the rotational motion of the spacer shaping control rod 210 as it passes through the threaded shaping passage 150. The surgeon, assistant or both would grip the spacer control sleeve 220 and the spacer shaping control rod 210 during the extension step (block 406). Since the spacer body 102 is cooled (block 404), the material is placed into the super-elastic state. This property significantly enhances the flexibility of the material. The optional retention features 130, 140, 142 are also drawn to a planar configuration. It is noted that the optional retention features 130, 140, 142 are oriented to enable insertion even when partially or completely extended, while resisting any motion in a reverse direction. When the spacer body 102 returns to its undeformed shape, the optional retention features 130, 140, 142 are extended, wherein the optional retention features 130, 140, 142 resist motion in a reverse direction. The surgeon inserts 299 the surgically implantable spacer 100 into the subject joint, preferably using the spacer expansion control mechanism assembly 200 to aid in guiding and positioning the surgically implantable spacer 100 into the target location (block 408). It is noted that the peripheral edge extending from the spacer insertion end 114 towards the spacer control end 112 is tapered providing a lead in shape. The lead in shape aids in the insertion process. Once the surgically implantable spacer 100 is properly positioned within the joint, the surgeon removes the spacer expansion control mechanism assembly 200 from the surgically implantable spacer 100 by unthreading the spacer control rod threaded segment 216 from the threaded shaping passage 150 (block 410). During or subsequent to the removal of the spacer expansion control mechanism assembly 200 from the surgically implantable spacer 100, the spacer body 102 is warmed to a temperature slightly above the transformation temperature (block 412) (such as near 98 degrees F. or a natural internal temperature of an individual), where the spacer body 102 is returned to shape memory a shape memory state. When in the shape memory state, the spacer body 102 returns to the undeformed configuration (block 414). An optional grafting process can be utilized to accelerate a fusing process. The surgically implantable spacer 100 can be set into location by a grafting process or other similar procedure. The grafting process would place an artificial retention material or initiate a natural formation of bone or other retaining materials in adhesive or mechanical grip with features of the spacer body 102. In the exemplary embodiment, the grafting or fusing processes (block 416) can utilize the threaded shaping passage 150, the blind receptacle 152, the segment defining slots 120, the retention features 130, 140, 142, and the like to secure the spacer body 102 in position.

Figure 12:
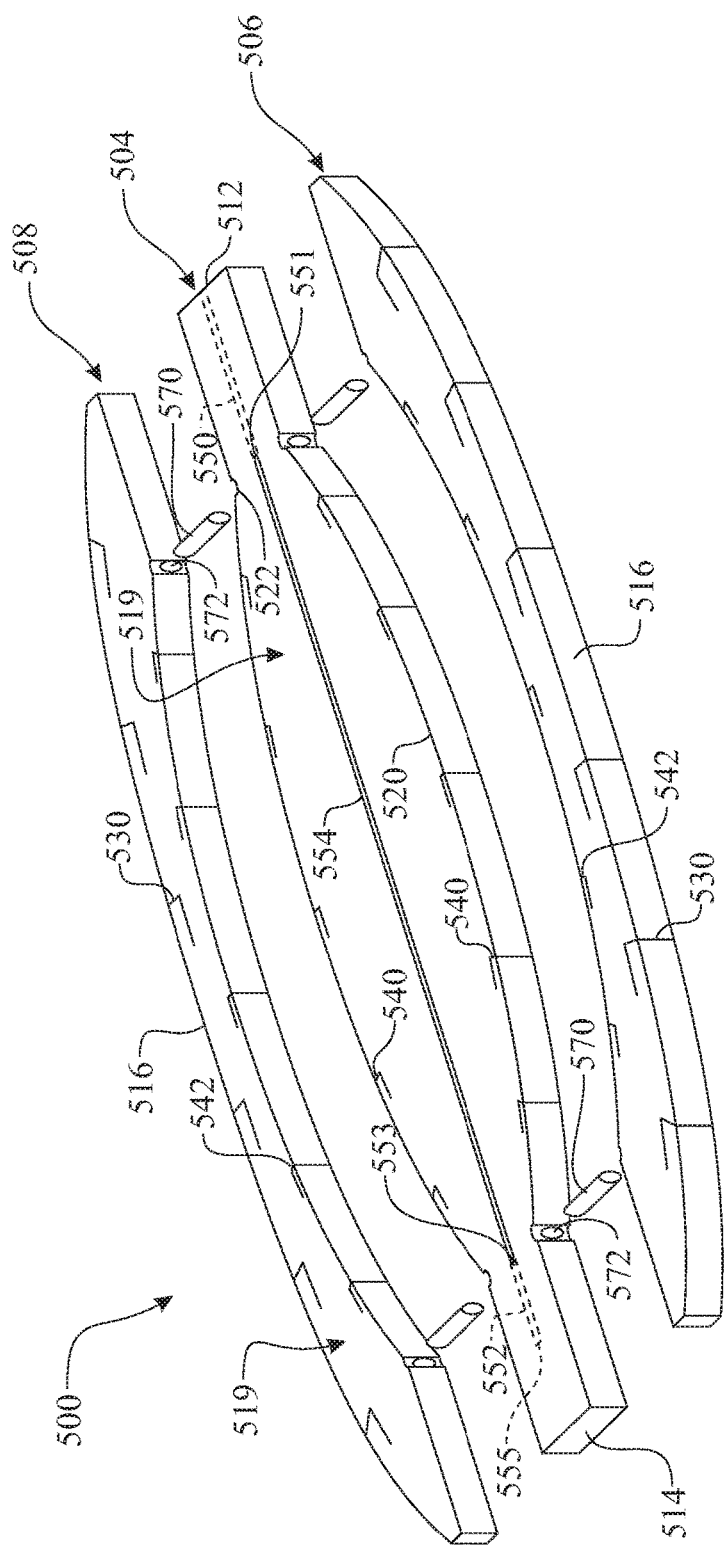
FIG. 12 presents an isometric exploded assembly view of an exemplary variant of the surgically implantable spacer.
Figure 13:
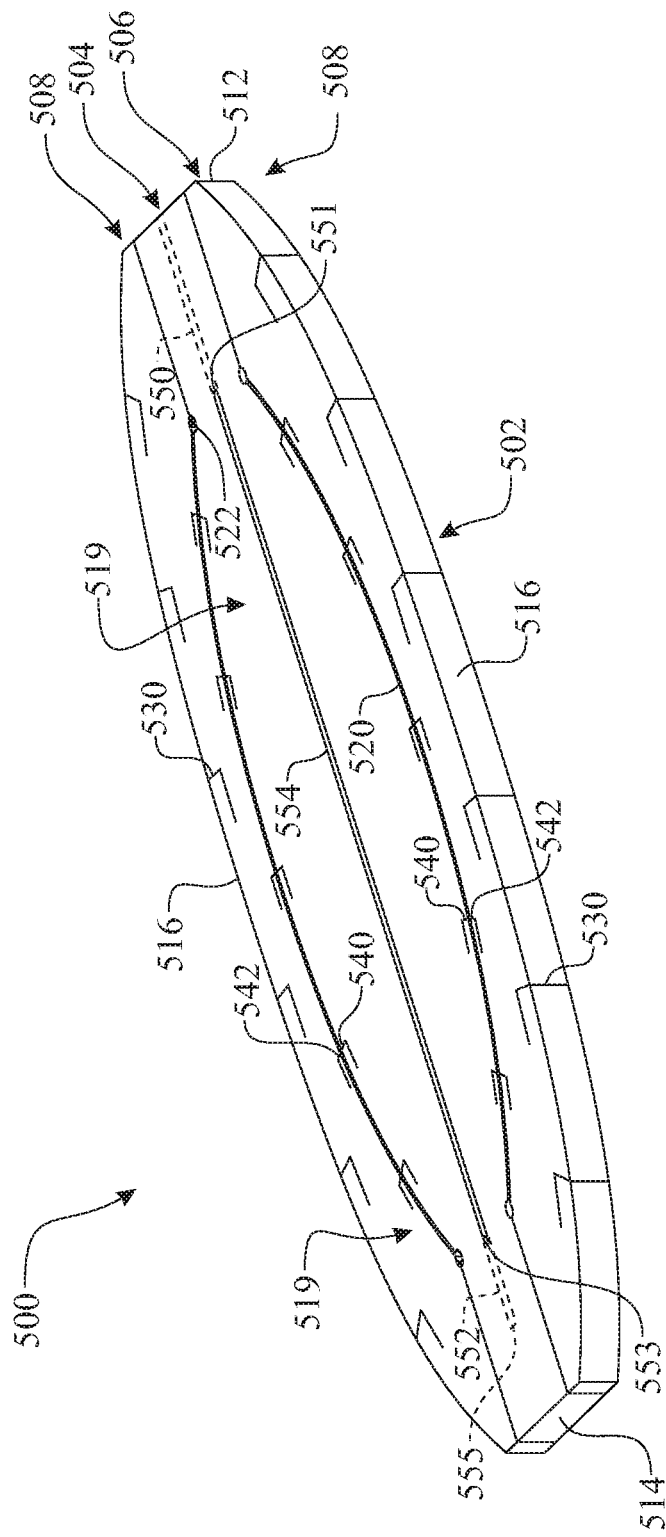
FIG. 13 presents an isometric assembled view of the surgically implantable spacer introduced in FIG. 12, the surgically implantable spacer illustrated in a planar configuration.

The surgically implantable spacer 100 relies upon deformation between each implanted spacer peripheral segment 110 and the implanted spacer inner segment 124. The surgically implantable spacer 100 can be modified by introducing a hinged version, referred to as a surgically implantable spacer 500 and illustrated in FIGS. 12 through 14. The surgically implantable spacer 500 includes a majority of the same features as the surgically implantable spacer 100. Like features of the surgically implantable spacer 500 and the surgically implantable spacer 100 are numbered the same except preceded by the numeral '5'.

Figure 14:
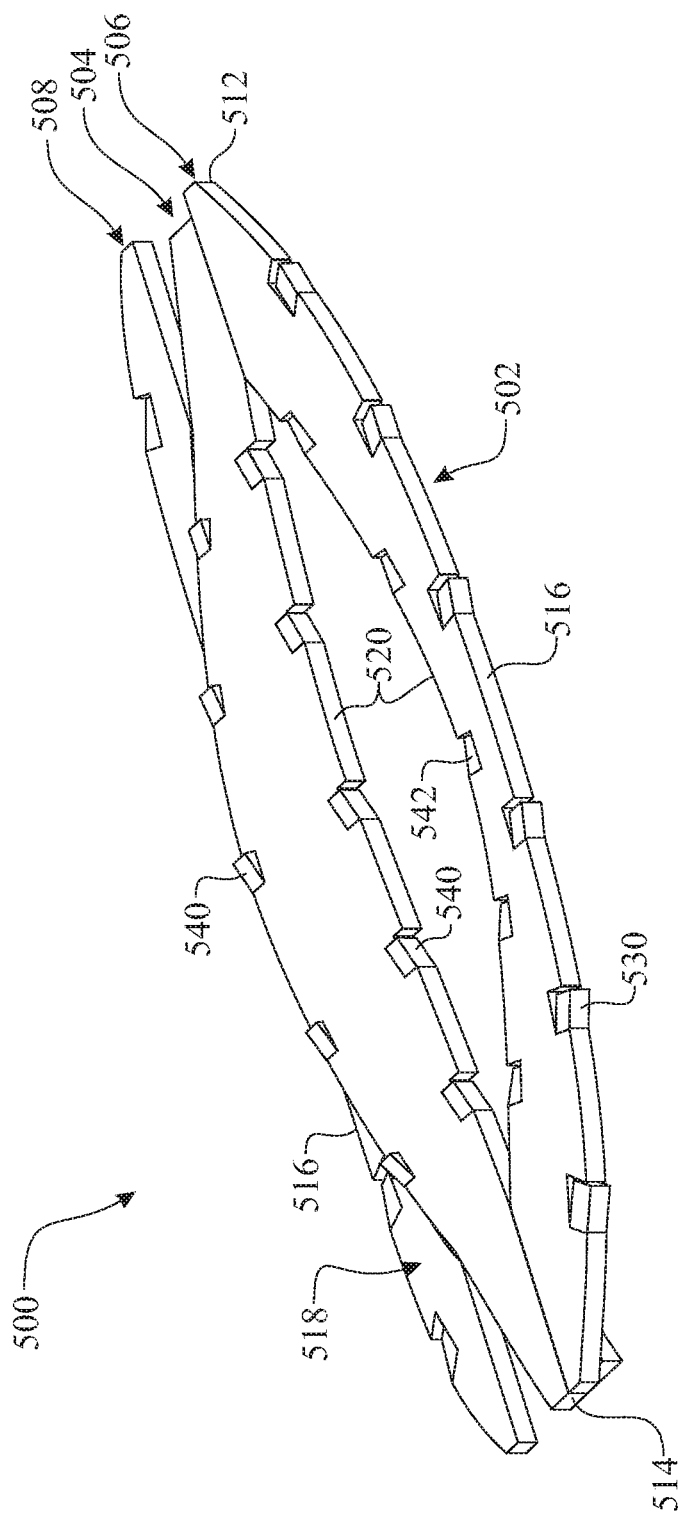
FIG. 14 presents an isometric assembled view of the surgically implantable spacer introduced in FIG. 12, the surgically implantable spacer illustrated in an expanded configuration.

A body of the surgically implantable spacer 500 comprises three pieces, more specifically, an implanted spacer central member 504, an implanted spacer first peripheral member 506, and an implanted spacer second peripheral member 508. The implanted spacer central member 504, implanted spacer first peripheral member 506, and implanted spacer second peripheral member 508 are pivotally assembled to one another by a set of assembly pins 570. Each of the implanted spacer central member 504, implanted spacer first peripheral member 506, and implanted spacer second peripheral member 508 includes an assembly pin receiving cavity 572 at each respective distal elongated end for receiving and retaining a respective portion of the assembly pin 570. The assembly pin 570 and the assembly pin receiving cavity 572 are pivot enabling elements, which, when assembled to one another, provide a pivoting function between the implanted spacer central member 504 and each of the implanted spacer first peripheral member 506 and the implanted spacer second peripheral member 508. The location of the assembly pin receiving cavity 572 can vary based upon the designer's options. The assembly pin 570 can be a single rod, pin, shaft, or axle when the assembly pin 570 is assembled through a location that would not interfere with the features for receiving and operating in conjunction with the spacer expansion control mechanism assembly 200. More specifically, in a configuration where the assembly pin 570 would not pass through or interfere with the threaded shaping passage (also referred to as a threaded spacing element or a proximal shaping element) 550 at the spacer control end 512 or a blind receptacle (also referred to as a distal shaping element) 552 at the spacer insertion end 514. The assembly pin 570 would be assembled and retained within each respective assembly pin receiving cavity 572 using any known and suitable retention method and/or design. In the exemplary embodiment illustrated herein, each assembly pin receiving cavity 572 is located at a small distance from each respective distal elongated end 512, 514 of the surgically implantable spacer 500. In this configuration, the distal edges of the implanted spacer central member 504, the implanted spacer first peripheral member 506 and the implanted spacer second peripheral member 508 would separate from one another when the surgically implantable spacer 500 is placed into an installed, expanded configuration, as shown in FIG. 14. The separation provides additional surface area and suitable geometric shapes for grafting and securing the surgically implantable spacer 500 in position at the implant site within the patient. The threaded shaping passage 550 can be a first spacer span control feature and the blind receptacle 552 can be a second spacer control feature. Alternatively, the blind receptacle 552 can be a first spacer span control feature and the threaded shaping passage 550 can be a second spacer control feature.

Alternatively, each assembly pin receiving cavity 572 can be located proximate each respective distal elongated end 512, 514 of the surgically implantable spacer 500. In this configuration, the distal edges of the implanted spacer central member 504, the implanted spacer first peripheral member 506 and the implanted spacer second peripheral member 508 would remain in close registration with one another.

The previous versions of the surgically implantable spacer 100, 500, employ the spacer expansion control mechanism assembly 200 to retain the surgically implantable spacer 100, 500 in a planar, compressed installation configuration. The spacer expansion control mechanism assembly 200 is adapted to apply an expansion force to the surgically implantable spacer 100, 500 along an elongated axis thereof. In an alternative retaining configuration, as exemplified by a surgically implantable spacer 600 illustrated in FIG. 15, a spacer compression retention mechanism assembly 700 is inserted through a series of bores formed extending parallel to and preferably in registration with a transverse axis of the surgically implantable spacer 600. The surgically implantable spacer 600 includes a majority of the same features as the surgically implantable spacer 500. Like features of the surgically implantable spacer 600 and the surgically implantable spacer 500 are numbered the same except preceded by the numeral '6'. Features not shown, such as the retention features 130, 140, 142 are understood to be optionally included.

Figure 15:
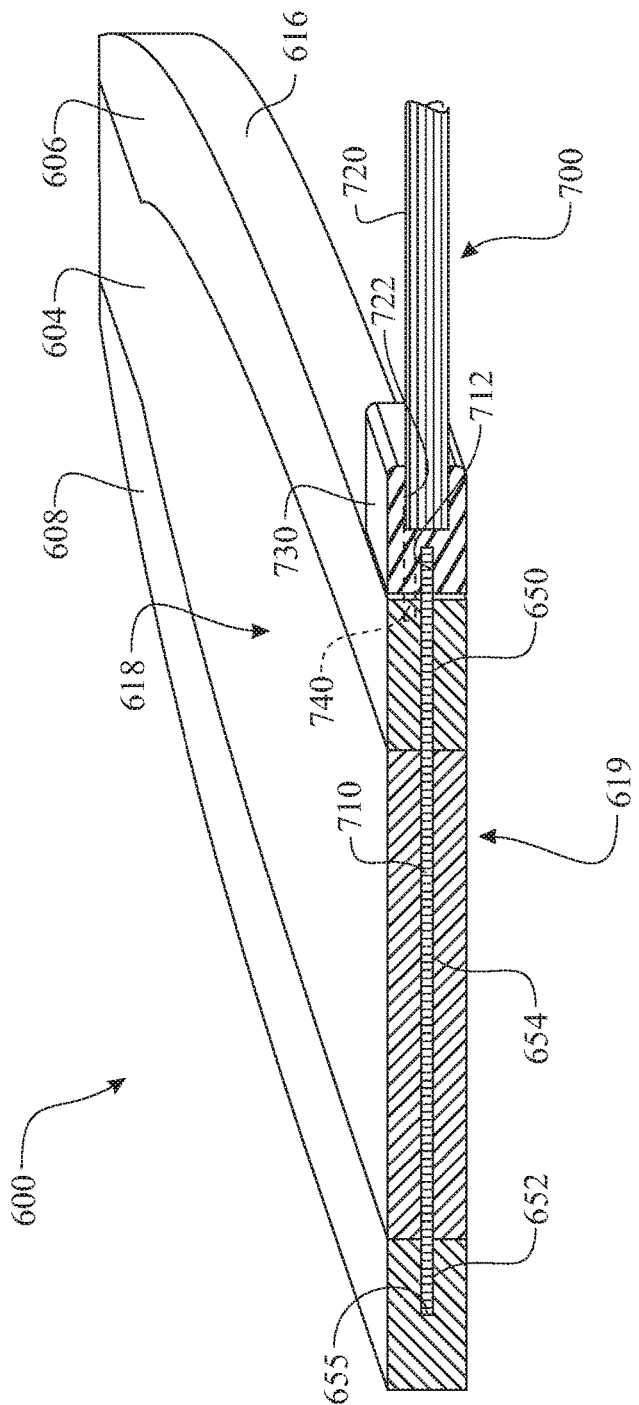
FIG. 15 presents a sectioned isometric assembly view of another exemplary variant of the surgically implantable spacer, the section being taken along a central transverse axis, illustrating a spacer compression retention mechanism assembly inserted through segments of the surgically implantable spacer, retaining the surgically implantable spacer in a planar configuration.

The spacer compression retention mechanism assembly 700 would be employed to retain the surgically implantable spacer 600 in a planar, compressed installation configuration, as illustrated in the sectioned view shown in FIG. 15.

Similar to the surgically implantable spacer 100, 500, the surgically implantable spacer 600 includes three members 604, 606, 608. A peripheral member compression retention through passage 650 is formed through the implanted spacer first peripheral member 606, extending between a spacer side edge 616 and a respective interior side edge (not identified). A central member compression retention through passage 654 is formed through the implanted spacer central member 604, extending between each of the pair of interior side edges (not identified). A peripheral member compression retention blind receptacle 652 is formed through the implanted spacer second peripheral member 608, extending from the interior side edge and terminating at a peripheral member compression retention blind receptacle end wall 655. Although less preferred, it is understood that the peripheral member compression retention blind receptacle 652 can pass through the implanted spacer second peripheral member 608, extending between the interior side edge and the respective spacer side edge 616 of the implanted spacer second peripheral member 608. A contacting surface of the spacer compression retention assembly end component 730 would govern the depth of penetration of the spacer compression retention control rod 710 through the surgically implantable spacer 600.

A spacer compression retention assembly end component 730 can optionally be included as an intermediary assembly component between a spacer compression retention control rod 710 and a spacer compression retention mechanism assembly handle 720 of the spacer compression retention mechanism assembly 700. A spacer compression retention control rod 710 is assembled to a spacer compression retention assembly end component 730 by any suitable assembly configuration. In the exemplary illustration, an assembly end of the spacer compression retention control rod 710 is inserted into a spacer compression retention control rod assembly bore 712 formed within the spacer compression retention assembly end component 730. Assembly of the spacer compression retention control rod 710 and the spacer compression retention assembly end component 730 can be completed by any suitable assembly design, including a mechanical assembly design, a threaded assembly design, a bonding agent, and the like. The assembly end of the spacer compression retention control rod 710 can be threaded to mate with a threaded surface formed within the spacer compression retention control rod assembly bore 712. Similarly, the spacer compression retention mechanism assembly handle 720 is assembled to the spacer compression retention assembly end component 730 by inserting an assembly end of the spacer compression retention mechanism assembly handle 720 into a spacer compression retention handle assembly bore 722 formed within the spacer compression retention assembly end component 730. Similarly, assembly of the spacer compression retention mechanism assembly handle 720 and the spacer compression retention assembly end component 730 can be completed by any suitable assembly design, including a mechanical assembly design, a threaded assembly design, a bonding agent, and the like.

The spacer compression retention control rod 710 can be of any suitable shape. In one variant, the spacer compression retention control rod 710 can have a circular cross sectional shape, wherein the circular cross sectional shape supports an easily formed circular shaped bores 650, 652, 654. Alternatively, the spacer compression retention control rod 710 can be shaped having a non-circular cross sectional shape and the bores 650, 652, 654 would be formed having shape that is compatible with the cross sectional shape of the spacer compression retention control rod 710. The non-circular cross sectional shape of the spacer compression retention control rod 710 would be used to aid in rotational orientation of the surgically implantable spacer 600 during insertion and placement of the surgically implantable spacer 600.

The spacer expansion control mechanism assembly 200 employs a spacer torsional control section 232 for aiding the medical professional in orienting the surgically implantable spacer 100, 500 during the insertion and placement of the surgically implantable spacer 100, 500 into the desired site of the patient. The spacer torsional control section 232 requires a design having a height or thickness that is greater than the thickness of the surgically implantable spacer 100, 500. The 720 introduces a spacer torsional control pin 740 as an alternative orientation assisting or rotational control feature for use during the insertion and placement of the surgically implantable spacer 600. The spacer torsional control pin 740 would extend outward from the spacer compression retention assembly end component 730 in a direction wherein an elongated axis of the spacer torsional control pin 740 that is parallel to an elongated axis of the spacer compression retention control rod 710. The spacer torsional control pin 740 would be inserted into a mating bore formed within a spacer side edge 616 of a surgically implantable spacer 600. In a preferred embodiment, the spacer compression retention mechanism assembly 700 would include a pair of spacer torsional control pins 740, each spacer torsional control pin 740 being placed equidistant to and in an opposite direction from a central axis of the spacer compression retention control rod 710.

In use, the surgically implantable spacer 600 would be prepared for use by compressing the implanted spacer central member 604 and the implanted spacer first peripheral member 606, 608 into a planar configuration. When placed into the planar configuration, each of the peripheral member compression retention through passage 650, the central member compression retention through passage 654, and the peripheral member compression retention blind receptacle 652 would be in linear registration with one another. The spacer compression retention control rod 710 would be inserted through the peripheral member compression retention through passage 650, continuing through the central member compression retention through passage 654 and extending into the peripheral member compression retention blind receptacle 652. It is noted that the natural or preformed arched shape of the implanted spacer central member 604, implanted spacer first peripheral member 606, and implanted spacer second peripheral member 608 would result in separation between the members 604, 606, 608. This separation would be restrained by the spacer compression retention control rod 710. This configuration would create apply a frictional force between the members 604, 606, 608 and the spacer compression retention control rod 710, thus providing some limited assistance for rotational orientation or control of the surgically implantable spacer 600 during the insertion and placement of the surgically implantable spacer 600 into the target site within the patient. Once properly placed, the spacer compression retention control rod 710 would be slideably removed from the surgically implantable spacer 600, enabling each of the members 604, 606, 608 of the surgically implantable spacer 600 to return to a natural or preformed arched shape.

Figure 16:
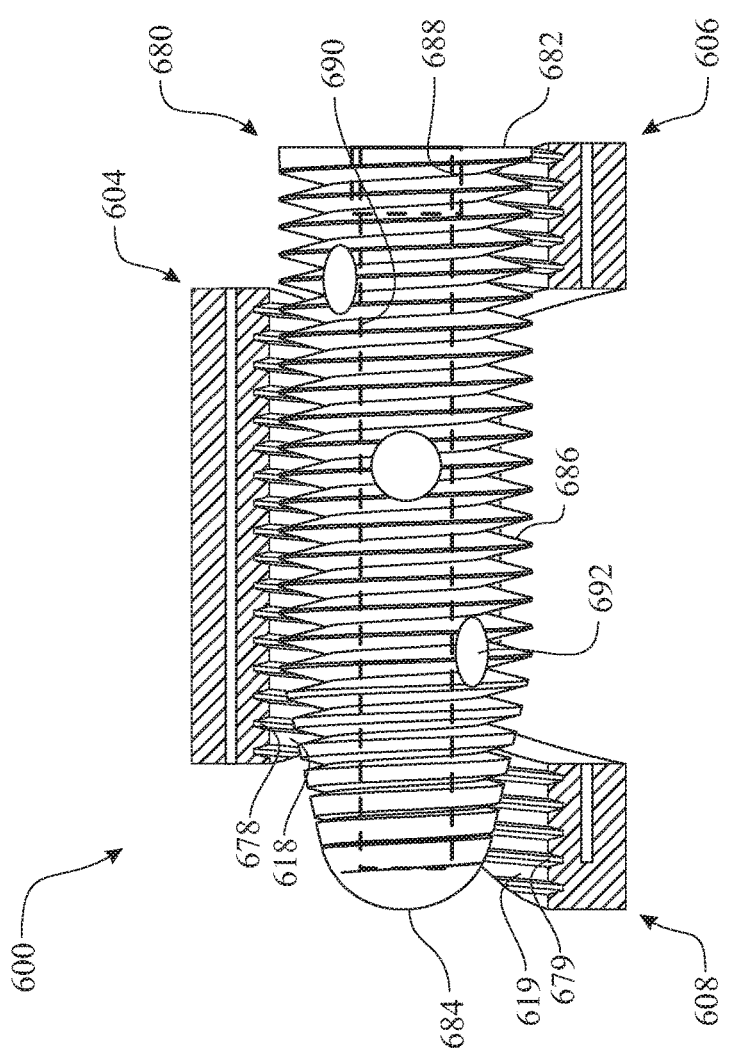
FIG. 16 presents a sectioned side elevation view of the surgically implantable spacer introduced in FIG. 15, the section being comparable to the section taken along section line 18-18 of FIG. 17, the illustration introducing a threaded spacing retention component.

The surgically implantable spacer 600 can employ any shape retention device to maintain the desired span between the interior surface 618 of the implanted spacer central member 604 and the opposite interior surfaces 619 of the implanted spacer first peripheral member 606 and the implanted spacer second peripheral member 608. In one exemplary solution, the span of the surgically implantable spacer 600 is maintained by a threaded spanner retention component 680, as illustrated in FIG. 16. The exemplary threaded spanner retention component 680 includes a threaded spanner retention component body 682 (preferably headless) having a threaded spanner retention component insertion driver receptacle 688 formed within a driving end of the threaded spanner retention component 680 and a threaded spanner retention component distal end 684 at an insertion end of the threaded spanner retention component 680. The threaded spanner retention component distal end 684 is preferably designed having a bulbous shape to aid in the insertion and spanning process, while minimizing any potential discomfort and/or complications for the patient. A spanner retention component threaded surface 686 would be formed about a cylindrical exterior surface of the threaded spanner retention component body 682. The threaded spanner retention component 680 can include any of a number of additional features to support the surgically implantable spacer 600. For example, the threaded spanner retention component 680 can include at least one grafting cavity 692 to enhance the retention of the implanted assembly. In another example, the threaded spanner retention component 680 can include a threaded spanner retention component interior cavity 690 to reduce weight of the implanted assembly. It is understood that the threaded spanner retention component interior cavity 690 can be formed to provide the functionality of the threaded spanner retention component insertion driver receptacle 688. The threaded spanner retention component 680 is one example of a spanner retention element.

The spacer upper surface 618 of the implanted spacer central member 604 and the spacer lower surface 619 of the implanted spacer first peripheral member 606 and the implanted spacer second peripheral member 608 can include threading, identified as a spacer central member upper surface threading 678 and a spacer peripheral member lower surface threading 679. The threaded surfaces can be confined to a central area of each of the members 604, 606, 608 or across the entire surface thereof. In use, the surgically implantable spacer 600 would be placed into the inserted, expanded configuration. The medical professional would determine the appropriate size required to maintain the desired span. The medical professional would select the appropriately sized threaded spanner retention component 680, more specifically, the threaded spanner retention component 680 having the desired diameter. A driver tool (not shown) can be inserted into the threaded spanner retention component insertion driver receptacle 688. The driver tool can be used to properly locate the threaded spanner retention component 680 in position. It is understood that the threaded spanner retention component insertion driver receptacle 688 should be sufficiently deep enough to provide sufficient control to the user while guiding the threaded spanner retention component 680 into the proper location. The threaded spanner retention component 680 would be inserted between the implanted spacer central member 604 and the implanted spacer peripheral members 606, 608. The threaded spanner retention component 680 would be rotated, engaging the spanner retention component threaded surface 686 with the spacer central member upper surface threading 678 and the spacer peripheral member lower surface threading 679, drawing the threaded spanner retention component 680 into position between the implanted spacer central member 604 and the implanted spacer peripheral members 606, 608 until the threaded spanner retention component 680 is centered about a width of the threaded spanner retention component 680.

Figure 17:
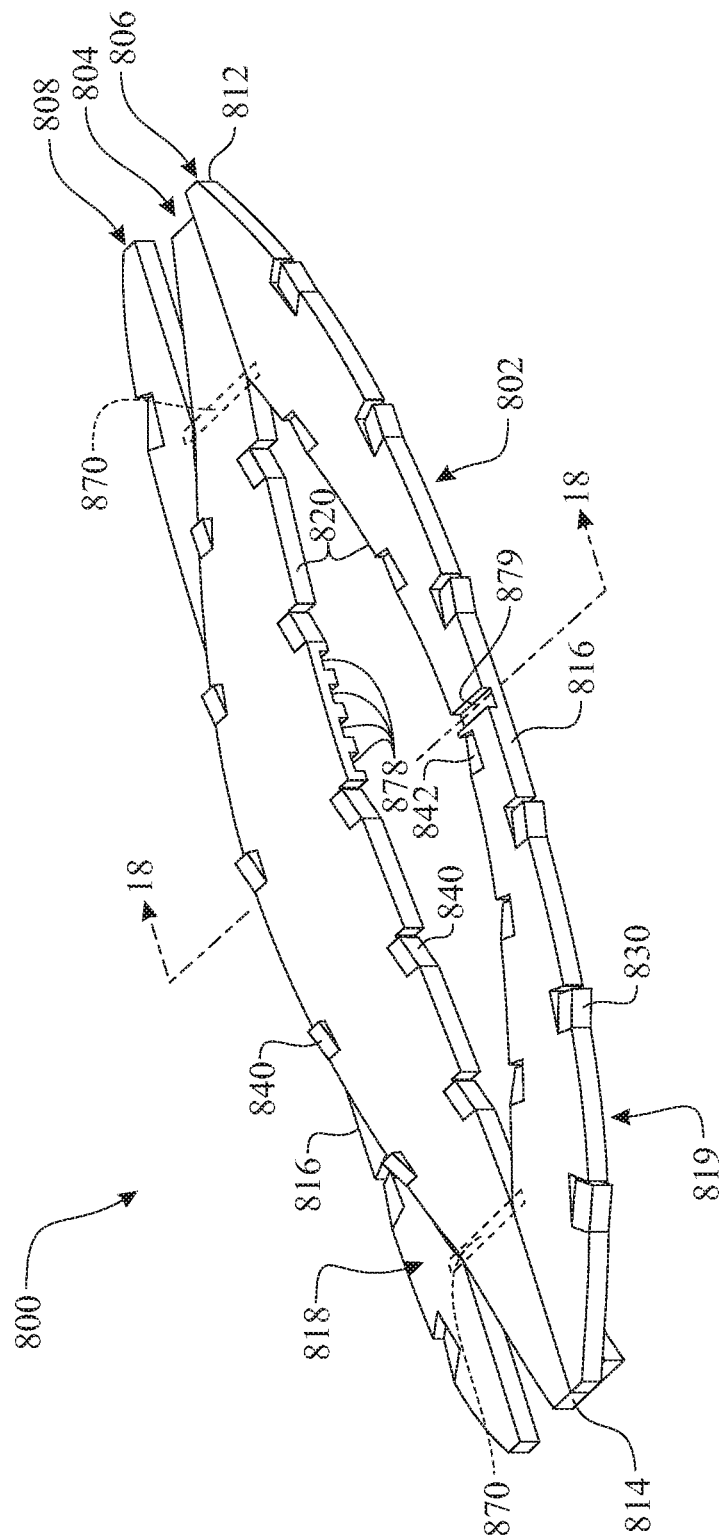
FIG. 17 presents an isometric view of another exemplary variant of the surgically implantable spacer.
Figure 18:
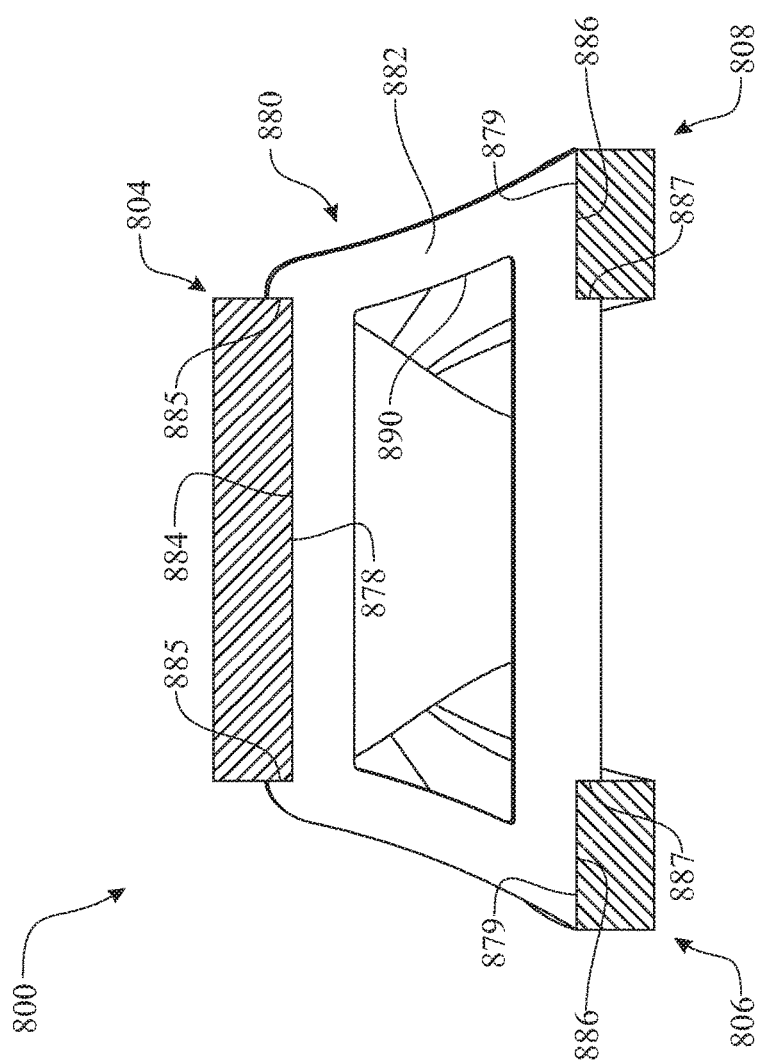
FIG. 18 presents a sectioned side elevation view of the surgically implantable spacer introduced in FIG. 17, the section taken along section line 18-18 of FIG. 17, the illustration introducing a planar spacing retention component.

The threaded spanner retention component 680 provides one exemplary spanning device. A surgically implantable spacer 800, as illustrated in FIGS. 17 and 18 introduces a second exemplary spanning device 880. The surgically implantable spacer 800 includes a majority of the same features as the surgically implantable spacer 500. Like features of the surgically implantable spacer 800 and the surgically implantable spacer 500 are numbered the same except preceded by the numeral '8'. The surgically implantable spacer 800 includes at least one spacer central member spanner receiving slot 878 formed in a spacer lower surface 819 of the implanted spacer central member 804 and at least one complimentary spacer peripheral member spanner receiving slot 879 formed in a spacer upper surface 818 of both the implanted spacer first peripheral member 806 and the implanted spacer second peripheral member 808.

The surgically implantable spacer 800 is fabricated by shaping a planar spanning retention component body 882 to include a central slot defined by a planar spanning retention component central receiving slot base supporting edge 884 and a pair of planar spanning retention component central receiving slot side edges 885 and a pair of edge slots, each edge slot defined by a planar spanning retention component outer receiving slot base supporting edge 886 and a respective planar spanning retention component outer receiving slot side edge 887. The central slot is located along one engaging edge of the planar spanning retention component 880 and the pair of edge slots is located along the second, opposite engaging edge of the planar spanning retention component 880. An optional planer spanning retention component aperture 890 can be formed passing through a central region of the planar spanning retention component body 882 to reduce weight and allow for grafting.

In the exemplary illustration, the surgically implantable spacer 800 includes a plurality of spacer central member spanner receiving slots 878 and a single spacer peripheral member spanner receiving slot 879. Each of the pair of edge slots are inserted into the respective spacer peripheral member spanner receiving slot 879. The central slot is inserted into one of the plurality of spacer central member spanner receiving slots 878. The plurality of spacer central member spanner receiving slots 878 enables the installation to accommodate different span distances. Each of the planar spanning retention component central receiving slot side edges 885 and the planar spanning retention component outer receiving slot side edges 887 restrains the planar spanning retention component 880 from any lateral movement.

Figure 19:
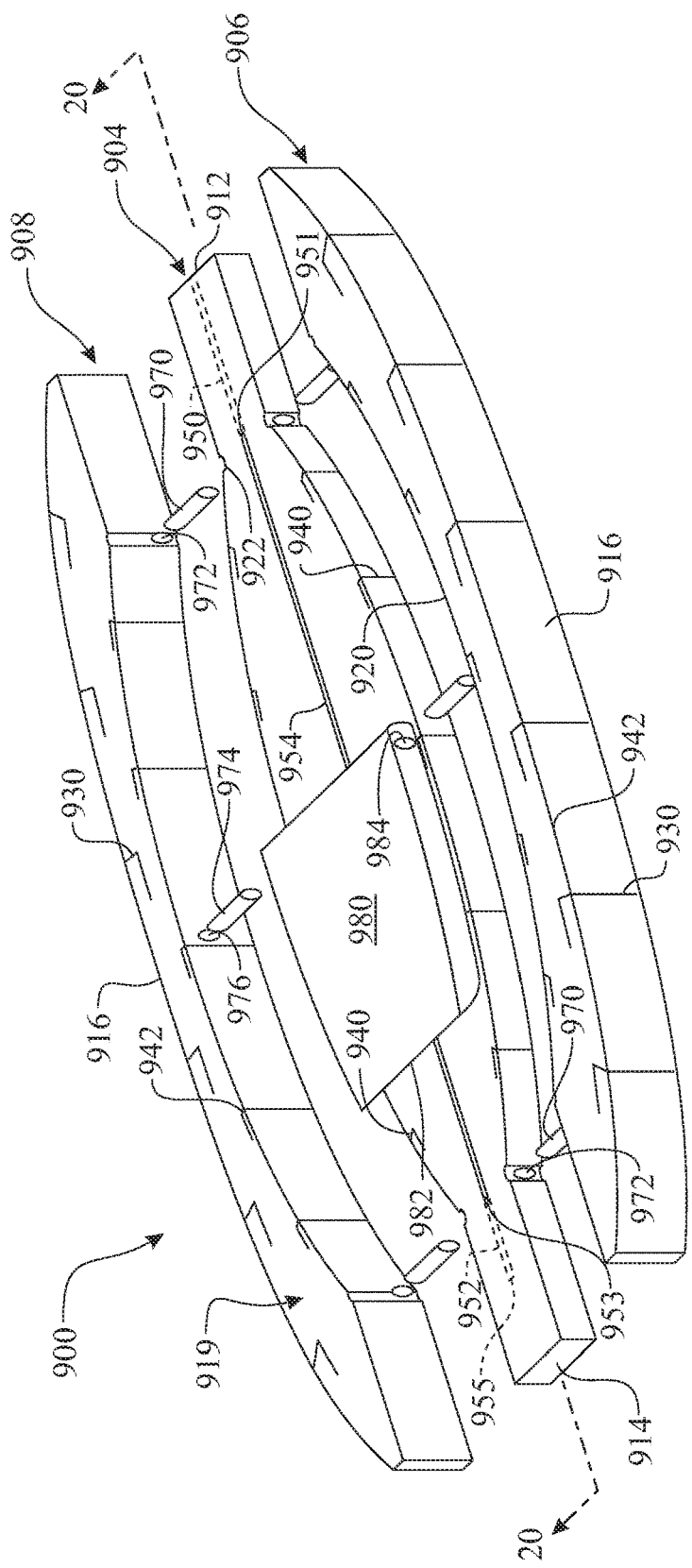
FIG. 19 presents an isometric exploded assembly view of another exemplary variant of the surgically implantable spacer, the surgically implantable spacer employing a pivotal spacing retention component.
Figure 20:
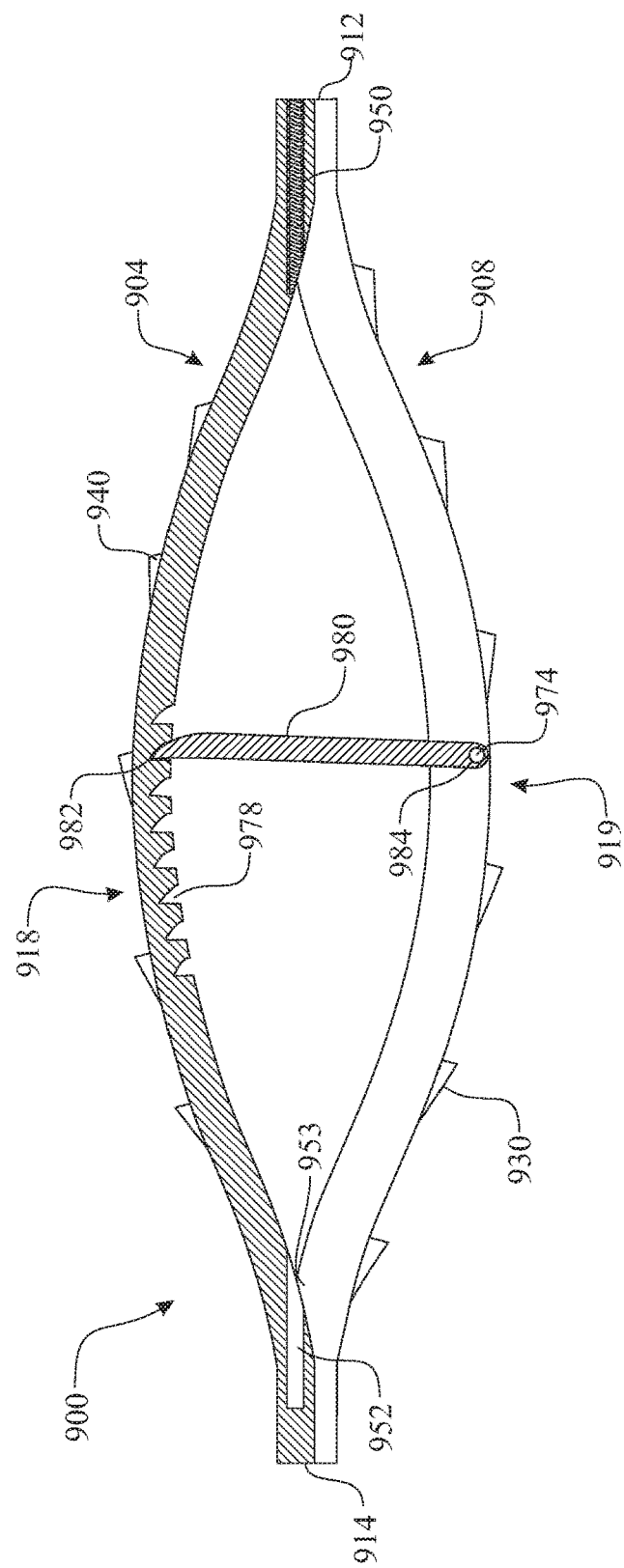
FIG. 20 presents a sectioned side elevation view of the surgically implantable spacer introduced in FIG. 19, the section taken along section line 20-20 of FIG. 19, the illustration detailing operation of the pivotal spacing retention component.

Each of the surgically implantable spacer 600, 800 employs an inserted and removable span retention component. A surgically implantable spacer 900, illustrated in FIGS. 19 and 20, employs a pivotal spanner component 980 to retain the desired span between the implanted spacer central member 904 and each of the implanted spacer first peripheral member 906 and the implanted spacer second peripheral member 908. The surgically implantable spacer 900 includes a majority of the same features as the surgically implantable spacer 500. Like features of the surgically implantable spacer 900 and the surgically implantable spacer 500 are numbered the same except preceded by the numeral '9', unless described otherwise herein. The pivotal spanner component 980 is pivotally assembled to each implanted spacer peripheral member 906, 908 using at least one pivotal spanner pivot pin 974. When using a single pivotal spanner pivot pin 974, the pivotal spanner pivot pin 974 would be inserted passing through the pivotal spanner pivot pin spanner receptacle 984 exposing each end, which are subsequently inserted into each respective pivotal spanner pivot pin spacer receptacle 976 of the respective implanted spacer peripheral member 906, 908. When using a pair of pivotal spanner pivot pins 974, one end of the pivotal spanner pivot pin 974 would be inserted into a pivotal spanner pivot pin spanner receptacle 984 of the pivotal spanner component 980 and the second, opposite end would be inserted into a pivotal spanner pivot pin spacer receptacle 976 of the respective implanted spacer peripheral member 906, 908. It is noted that each implanted spacer peripheral member 906, 908 can be fabricated of a material having a thickness that is greater than a thickness of the material used to fabricate the implanted spacer central member 904. Each pivotal spanner pivot pin spacer receptacle 976 would be located off center to provide a proper clearance for assembly and operation of the pivotal spanner component 980 to the surgically implantable spacer 900. The pivotal spanner component 980 would have a dimension extending radially from the pivot axis defined by the pivotal spanner pivot pin 974 that is compatible with a span of the surgically implantable spacer 900 when the surgically implantable spacer 900 is in an inserted, expanding configuration. A pivotal spanner component distal edge 982 of the pivotal spanner component 980 would be positioned against a spacer lower surface 919 of the implanted spacer central member 904 to create a wedge between the implanted spacer peripheral members 906, 908 and the implanted spacer central member 904. At least one pivotal spanner component distal edge engagement feature 978 can be formed within the spacer lower surface 919 (interior surface) of the implanted spacer central member 904. Each of the at least one pivotal spanner component distal edge engagement feature 978 is preferably shaped to receive and retain the pivotal spanner component distal edge 982 of the pivotal spanner component 980 in position during use of the surgically implantable spacer 900. A plurality of pivotal spanner component distal edge engagement features 978 provides adjustability to the overall retained span between the implanted spacer central member 904 and each of the implanted spacer peripheral members 906, 908. The pivotal spanner component distal edge 982 can be formed to aid in the rotational movement of the pivotal spanner component 980 during the process for positioning the spanning support element into the proper position. In the exemplary illustration, the pivotal spanner component distal edge 982 is formed having an off centered tapered edge to aid in the rotation process. The tapered edge acts to guide the pivotal spanner component distal edge 982 out of a previous pivotal spanner component distal edge engagement feature 978 and into an adjacent pivotal spanner component distal edge engagement feature 978. This design would be analogous to a ratcheting mechanism.

Each of the surgically implantable spacer 100, 500, 800, 900 includes a fixed threaded shaping passage 150 and blind receptacle 152. Using the surgically implantable spacer 100 as an example, the threaded shaping passage 150 and the blind receptacle 152, being fixed, dictate that the ends of the surgically implantable spacer 100 remain in a linear arrangement with one another. In the hinged configuration, using the surgically implantable spacer 500 as an example, this dictation could impact the ease of use of the spacer expansion control mechanism assembly 200.

Figure 21:
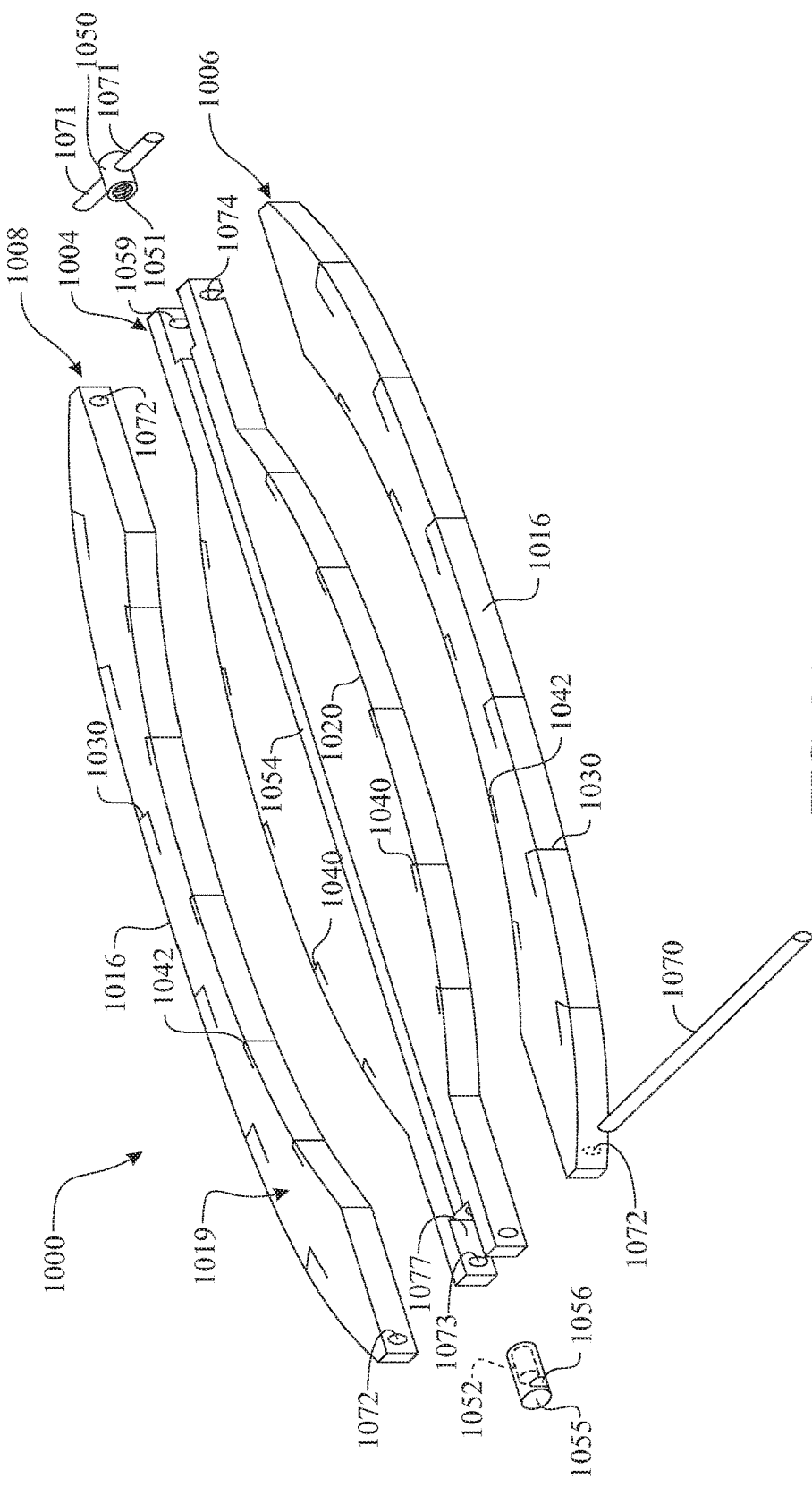
FIG. 21 presents an isometric exploded assembly view of another exemplary variant of the surgically implantable spacer, the surgically implantable spacer comprising a plurality of spacer body segments pivotally assembled to one another using a set of pivot pin assemblies, the pivot pin assemblies include pivotal shaping control rod engaging features which pivot to remain in linear alignment for the spacer shaping control rod.

A surgically implantable spacer 1000, illustrated in FIG. 21, introduces a pivotal option for the threaded shaping passage 150 and the blind receptacle 152, referred to as a pivotal threaded expansion shaping element 1050 and an expansion shaping element blind receptacle 1052. The surgically implantable spacer 1000 includes a majority of the same features as the surgically implantable spacer 500. Like features of the surgically implantable spacer 1000 and the surgically implantable spacer 500 are numbered the same except preceded by the numeral '10', unless described otherwise herein.

The key distinction between the surgically implantable spacer 500 and the surgically implantable spacer 1000 is the inclusion of a pivotal variant of the threaded shaping passage 150 and the blind receptacle 152. The blind receptacle 152 is replaced by a pivotal blind receptacle expansion shaping element 1055. An expansion shaping element blind receptacle 1052 is formed extending axially inward from one end of the pivotal blind receptacle expansion shaping element 1055. A bored expansion shaping element hinge pin receiving bore 1056 is formed extending radially through the pivotal blind receptacle expansion shaping element 1055. In the illustrated variant, the expansion shaping element blind receptacle 1052 terminates prior to the bored expansion shaping element hinge pin receiving bore 1056. It is understood that the expansion shaping element blind receptacle 1052 can pass through the pivotal blind receptacle expansion shaping element 1055, where the inserted assembly pin 1070 would provide the same function as the terminal end of the blind cavity.

A pivotal shaping element clearance 1077 extends inward from a respective end of the implanted spacer central member 1004. The pivotal shaping element clearance 1077 provides a clearance for the pivotal blind receptacle expansion shaping element 1055. The pivotal shaping element clearance 1077 should be sized to accommodate a rotational motion of the expansion shaping element blind receptacle 1052 when pivotally assembled to the surgically implantable spacer 1000 within the pivotal shaping element clearance 1077. A pair of assembly hinge pin receiving bores 1073 is formed extending through each leg defined by the pivotal shaping element clearance 1077. An assembly pin 1070 is of a sufficient length to assemble an implanted spacer first peripheral member 1006 and an implanted spacer second peripheral member 1008 to an implanted spacer central member 1004. The pivotal blind receptacle expansion shaping element 1055 would be assembled to the surgically implantable spacer 1000 by locating the pivotal blind receptacle expansion shaping element 1055 within the pivotal shaping element clearance 1077 and inserting the assembly pin 1070 through the bored expansion shaping element hinge pin receiving bore 1056. Each distal or free end of the assembly pin 1070 would be inserted into the respective assembly hinge pin receiving cavity 1072. The assembly pin 1070 would be retained in position in accordance with any suitable pin retention method known by those skilled in the art.

Similarly, the threaded shaping passage 150 is replaced by a pivotal threaded expansion shaping element 1050. An expansion shaping element threading 1051 is formed about an interior surface of a bore that is preferably concentrically arranged within the body of the pivotal threaded expansion shaping element 1050. The pivotal threaded expansion shaping element 1050 is pivotally assembled to the surgically implantable spacer 1000 by a pair of segmented assembly pin 1071. Each segmented assembly pin 1071 extends radially from the pivotal threaded expansion shaping element 1050. A free end of each segmented assembly pin 1071 is inserted into a respective assembly hinge pin receiving cavity 1072 formed through an interior side edge of the respective implanted spacer peripheral members 1006, 1008. Each segmented assembly pin 1071 would be retained in position in accordance with any suitable pin retention method known by those skilled in the art. Each segmented assembly pin 1071 would be assembled to the pivotal threaded expansion shaping element 1050 in a manner to avoid interfering with the expansion shaping element threading 1051 passing therethrough. The proximate end of the implanted spacer central member 1004 would be assembled to the segmented assembly pin 1071 using a bore (similar to the assembly hinge pin receiving bore 1073), an assembly hinge pin receiving slot 1074 (as illustrated) or any other suitable assembly configuration. The assembly hinge pin receiving slot 1074 enables a rotational assembly process of the implanted spacer central member 1004 to each segmented assembly pin 1071 following an assembly of each segmented assembly pin 1071 to a respective implanted spacer peripheral member 1006, 1008. This configuration is adapted for preassembly of the pair of segmented assembly pins 1071 to the pivotal threaded expansion shaping element 1050.

The surgically implantable spacer 1000 can be modified by forming reverse female threads within the expansion shaping element blind receptacle 1052 of the pivotal blind receptacle expansion shaping element 1055. Similarly, the spacer control rod extension segment 218 of the spacer expansion control mechanism assembly 200 would include reverse male threads. The reverse male threads of the spacer control rod extension segment 218 would engage with the reverse female threads within the receptacle 1052. This configuration would introduce a tensile force in addition to the expansion force applied at the pivotal blind receptacle expansion shaping element 1055.

In another variant, the threaded sections 1051, 1052 can be replaced with a ratcheting design. The ratcheting design would engage with ratchet latching features on the spacer shaping control rod 210 of the spacer expansion control mechanism assembly 200.

A portion of the spacer expansion control mechanism assembly 200 can be adapted to remain within the surgically implantable spacer 1000 (or any other applicable version) providing support for the spacing between the implanted spacer central member 1004 and each of the implanted spacer first peripheral member 1006 and implanted spacer second peripheral member 1008. A crimping mechanism can be employed to retain one of more of the features of the surgically implantable spacer 1000 (or any other applicable version) in position once the surgically implantable spacer 1000 is implanted into the patient.

Each of the previous variants 100, 500, 600, 800 employs a separate mechanical component to retain the span between the implanted spacer central segment or member and each of the implanted spacer peripheral segments or members.

It is also recognized that at least one spacer segment or member can incorporate a self shape-retaining feature. Examples of variants of self shape-retaining features are taught in FIGS. 22 through 27. Each variant includes at least one cantilevered hook 1174, 1274, 1374. In an extended, planar configuration (FIGS. 22, 24, 26), the cantilevered hook 1174, 1274, 1374 remains free. As the self-shaping spacer member is reconfigured into an arched shape (FIGS. 23, 25, 27), each at least one cantilevered hook 1174, 1274, 1374 would engage with a respective latching feature 1165, 1265, 1365. Each cantilevered hook 1174, 1274, 1374 includes a cantilevered hook contacting surface 1175, 1275, 1375; each respective latching feature 1165, 1265, 1365 includes a latching feature contacting surface 1165, 1265, 1365. In a latched configuration, at least one cantilevered hook contacting surface 1175, 1275, 1375 is positioned to engage with a respective latching feature contacting surface 1165, 1265, 1365.

The latching feature 1165, 1265, 1365 would be based upon the selected variant.

Figure 22:
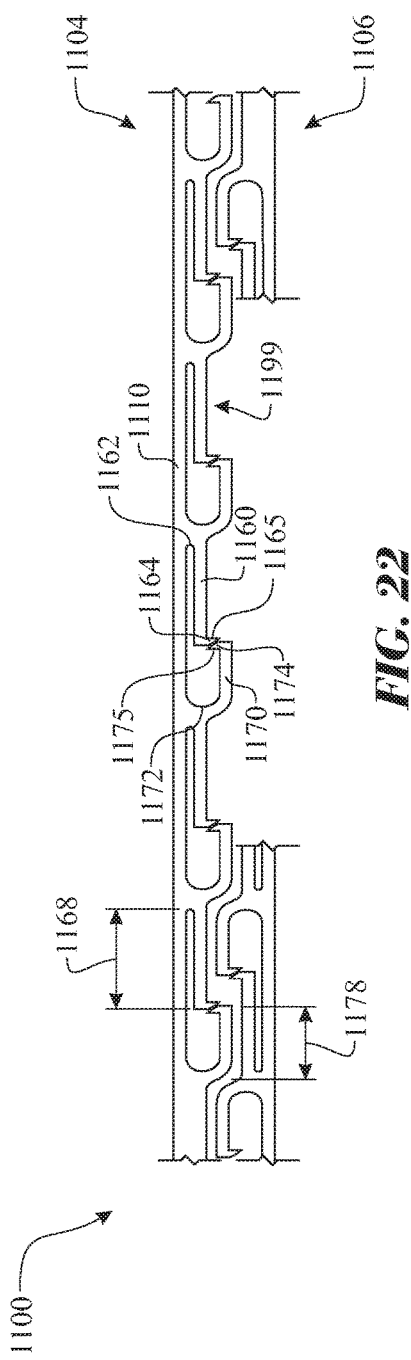
FIG. 22 presents a side elevation partial view of another exemplary surgically implantable spacer, the surgically implantable spacer comprising a pair of self locking surgically implantable spacer segments, wherein the self locking feature includes a plurality of cantilevers hooks and mating cantilevers hooks, the illustration presenting the surgically implantable spacer in a pre-insertion, collapsed, planar configuration.
Figure 23:
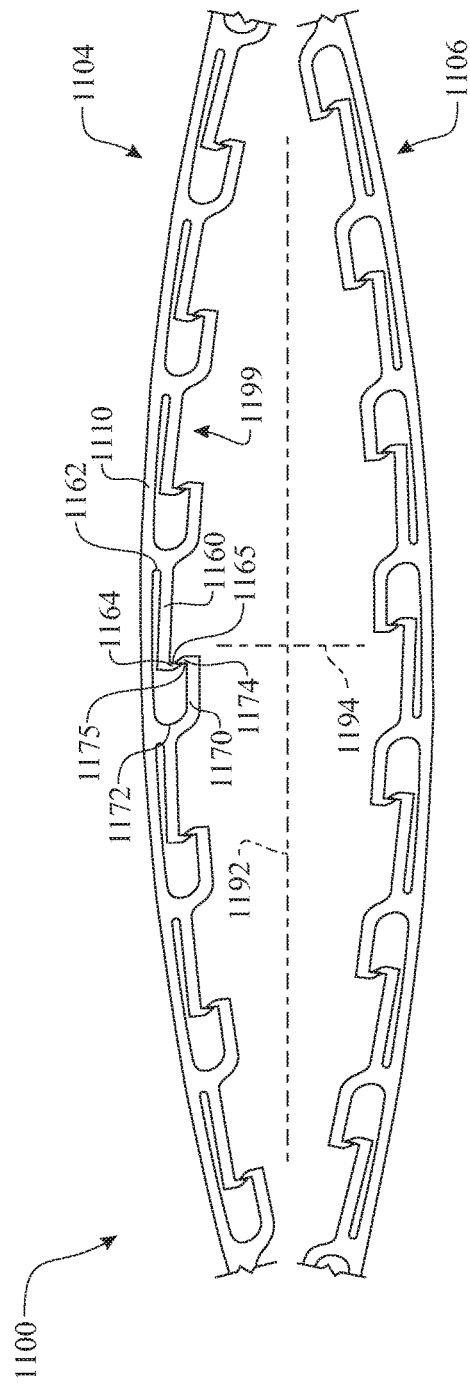
FIG. 23 presents a side elevation partial view of the exemplary surgically implantable spacer originally introduced in FIG. 22, the illustration presenting the surgically implantable spacer in an inserted, expanded configuration.

A surgically implantable spacer 1100 is illustrated in FIGS. 22 and 23. The surgically implantable spacer 1100 would be configured including at least an implanted first spacer member 1104 and an implanted second spacer member 1106. The implanted first spacer member 1104 and the implanted second spacer member 1106 can be configured as an upper implantable space and a lower implantable spacer, each having a like peripheral shape. The implanted first spacer member 1104 and the implanted second spacer member 1106 would be pivotally assembled to one another using any suitable pivot or hinged design. This configuration provides two substantially smooth exterior surfaces for ease of insertion and placement of the surgically implantable spacer 1100 into the desired location within the patient's joint. Alternatively, the surgically implantable spacer 1100 can include one implanted first spacer member 1104 and a pair of implanted second spacer member 1106, wherein the implanted first spacer member 1104 would be configured similar to the implanted spacer central member 504 and the implanted second spacer member 1106 would be configured similar to the implanted spacer first peripheral member 506 and the implanted spacer second peripheral member 508. Each of the spacer members 1104, 1106 include a spacer frame segment 1110 extending along an outer region thereof. The outer surface of the spacer frame segment 1110 is a generally smooth, planar surface. The inner latch cantilevered arm hook 1174 is formed at a free end of an inner latch cantilevered arm 1170. The inner latch cantilevered arm 1170 extends generally parallel to a longitudinal axis of the implanted first spacer member 1104. An attachment end of the inner latch cantilevered arm 1170 is preferably formed having an arched shape. This arched shape provides optimal flexure, while maintaining reliability and strength. The flexibility of the inner latch cantilevered arm 1170 is a function of an inner latch cantilevered arm length 1178 and a shape of an inner latch cantilevered arm connectivity formation 1172. The larger the inner latch cantilevered arm length 1178, the greater the flexure of the inner latch cantilevered arm length 1178. The inner latch cantilevered arm connectivity formation 1172 is preferably rounded in shape for reliability, as the curved shape minimizes stress fracture. The inner latch cantilevered arm length 1178 is also considered to ensure that the inner latch cantilevered arm hook 1174 remains engaged with the outer latch cantilevered arm hook 1164. Excessive flexure introduces a risk of uncoupling between the inner latch cantilevered arm hook 1174 and the outer latch cantilevered arm hook 1164.

In the surgically implantable spacer 1100, the outer latch cantilevered arm hook 1164 is supported by an outer latch cantilevered arm 1160. Like the inner latch cantilevered arm 1170, flexibility of the outer latch cantilevered arm 1160 is governed by an outer latch cantilevered arm length 1168 and a shape of an outer latch cantilevered arm connectivity formation 1162. The outer latch cantilevered arm connectivity formation 1162 is preferably rounded in shape for reliability, as the curved shape minimizes stress fracture. A combination of the flexibility of each of the inner latch cantilevered arm 1170 and the outer latch cantilevered arm 1160 must be considered when designing the spacer members 1104, 1106. The inner latch cantilevered arm hook 1174 is preferably oriented extending towards the spacer frame segment 1110. The outer latch cantilevered arm 1160 is located between the spacer frame segment 1110 and the inner latch cantilevered arm 1170. The outer latch cantilevered arm hook 1164 is oriented extending towards the inner latch cantilevered arm 1170. The spacer frame segment 1110 provides the support across a length of the spacer members 1104, 1106. The formation of the profile of each spacer member 1104, 1106 can be fabricated using an Electrical Discharge Machining (EDM) process, sometimes referred to as a wire-cutting Electrical Discharge Machining process.

It is preferred to provide a surgically implantable spacer 1100 having a pair of planar or substantially planar, smooth exterior surfaces for ease of insertion and placement thereof within the joint of the patient. The formation of the inner latch cantilevered arm 1170 and the mating outer latch cantilevered arm 1160 creates a recessed formation 1199. The surgically implantable spacer 1100 can utilize like formations for each of the implanted first spacer member 1104 and the implanted second spacer member 1106. The implanted first spacer member 1104 would be assembled in a first orientation and the implanted second spacer member 1106 would be assembled in a second orientation, where the second orientation is mirrored about a longitudinal mirror plane 1192, which is a plane parallel to the planar external surface of the implanted first spacer member 1104 and mirrored about a lateral mirror plane 1194, which is plane perpendicular to the planar external surface of the implanted first spacer member 1104 extending along an axis transverse to a longitudinal axis of the implanted first spacer member 1104. This arrangement positions each inner latch cantilevered arm 1170 into each respective recessed formation 1199. The arrangement provides external surfaces that are substantially planar and smooth, while minimizing any overall thickness of the surgically implantable spacer 1100 when placed into a planar, insertion configuration, as shown in FIG. 22.

In use, the surgically implantable spacer 1100 is initially positioned in a collapsed, planar configuration, as illustrated in FIG. 22. Each inner latch cantilevered arm hook 1174 would be uncoupled or disengaged from each outer latch cantilevered arm hook 1164. The medical professional would locate the collapsed surgically implantable spacer 1100 (FIG. 22) into the proper position between the joint. Once positioned, the medical professional would force the surgically implantable spacer 1100 to expand into the expanded arched configuration (FIG. 23) by drawing two distal ends towards one another. Drawing the two distal ends towards one another causes the planar shaped spacer members to arch. The arching shape of the spacer members 1104, 1106 draws the inner latch cantilevered arm hook contact surface 1175 of the inner latch cantilevered arm hook 1174 towards engagement with the outer latch cantilevered arm hook contact surface 1165 of the outer latch cantilevered arm hook 1164. The flexibility of the inner latch cantilevered arm 1170 and the outer latch cantilevered arm 1160 enables the inner latch cantilevered arm hook 1174 and the outer latch cantilevered arm hook 1164 to positionally adjust and slideably pass across one another. As the inner latch cantilevered arm hook 1174 and the outer latch cantilevered arm hook 1164 slideably pass across one another, the inner latch cantilevered arm hook contact surface 1175 and the outer latch cantilevered arm hook contact surface 1165 engage with one another, locking the spacer members 1104, 1106 into the arched shape. Details of the design can be adapted to determine the resulting arch of the spacer members 1104, 1106. Additionally, varying the number of engagements of inner latch cantilevered arm hook 1174 and outer latch cantilevered arm hook 1164 also can be used to increase or decrease the arch; more engagements the greater the arch, less engagements, the lower the arch.

A surgically implantable spacer 1200, illustrated in FIGS. 24 and 25, is a slight variant of the surgically implantable spacer 1100. The surgically implantable spacer 1200 includes a majority of the same features as the surgically implantable spacer 1100. Like features of the surgically implantable spacer 1200 and the surgically implantable spacer 1100 are numbered the same except preceded by the numeral '12', unless described otherwise herein. The implanted first spacer member 1204 of the surgically implantable spacer 1200 differs from the implanted first spacer member 1104 of the surgically implantable spacer 1100 in that the outer latch cantilevered arm hook 1264 is not located at a free end of a cantilevered arm. The outer region of the spacer member 1204, 1206 comprises a spacer frame latching segment 1210 and a spacer frame segment 1211. The inner latch cantilevered arm 1270 is cantilevered, extending substantially parallel to and on an interior side of the spacer frame latching segment 1210. The outer latch cantilevered arm hook 1264 is formed within a lower edge or surface of a spacer frame segment 1211 proximate the mating inner latch cantilevered arm hook 1274. This configuration introduces a spacer frame segment 1211 spanning between adjacent inner latch cantilevered arms 1270. The spacer frame segment 1211 provides sufficient material for optionally including a plurality of retention features 1240. The spacer frame latching segment 1210 can have a thickness that is less than the spacer frame segment 1211, a thickness that is the same as the spacer frame segment 1211, or a thickness that is greater than the spacer frame segment 1211. The thickness of each of the spacer frame latching segment 1210 and the spacer frame segment 1211 would be adapted to control a bending of the spacer member 1204, 1206. In the exemplary variant, the implanted second spacer member 1206 is provided as a planar sheet of material, exclusive of the arch forming retention features. The implanted second spacer member 1206 can optionally include a plurality of circumferential outer edge retention features 1230. The planar implanted second spacer member 1206 is illustrated as one optional configuration. Alternatively, based upon the concept used for designing the surgically implantable spacer 1100, the designer can opt to use a formation of the surgically implantable spacer 1200 utilizing a pair of implanted first spacer member 1204 arranged to have a likeness to the implanted first spacer member 1204.

Figure 26:
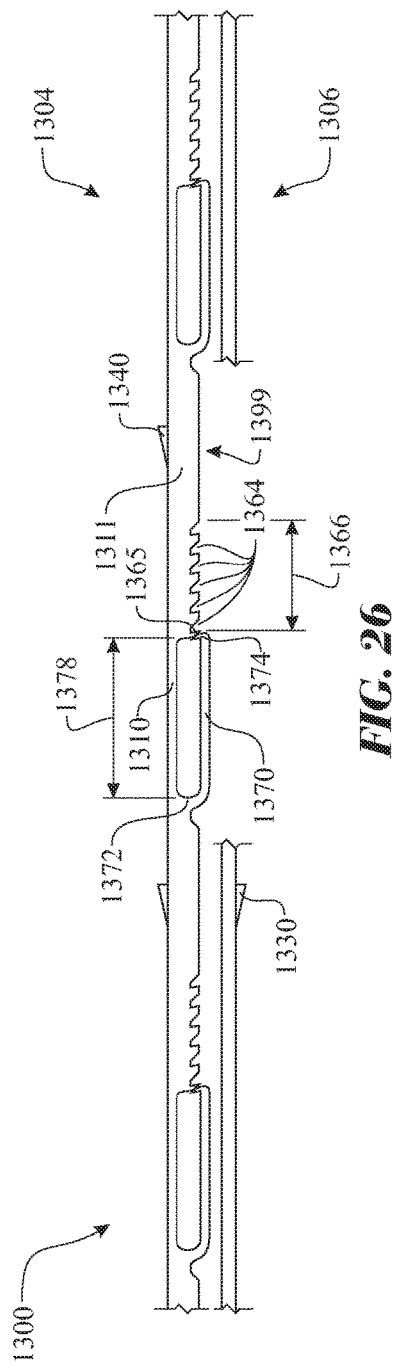
FIG. 26 presents a side elevation partial view of another exemplary surgically implantable spacer, the surgically implantable spacer comprising a pair of self locking surgically implantable spacer segments, wherein the self locking feature includes a plurality of cantilevers hooks and a mating series of slots, the illustration presenting the surgically implantable spacer in a pre-insertion, collapsed, planar configuration.
Figure 27:
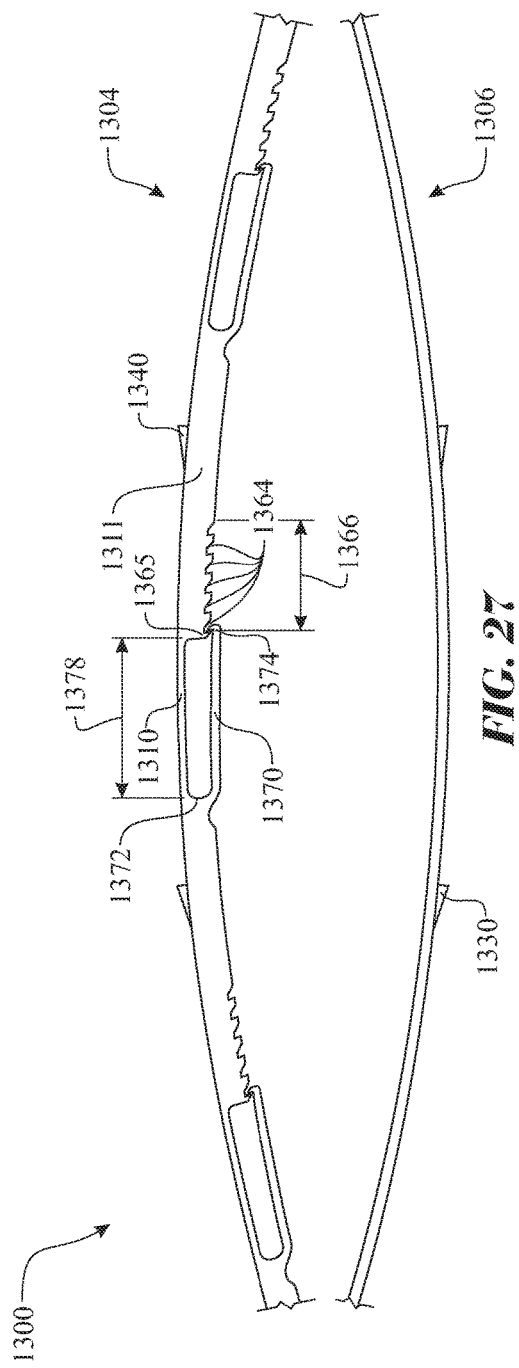
FIG. 27 presents a side elevation partial view of the exemplary surgically implantable spacer originally introduced in FIG. 26, the illustration presenting the surgically implantable spacer in an inserted, expanded configuration.

A surgically implantable spacer 1300, illustrated in FIGS. 26 and 27, is a slight variant of the surgically implantable spacer 1200. The surgically implantable spacer 1300 includes a majority of the same features as the surgically implantable spacer 1200. Like features of the surgically implantable spacer 1300 and the surgically implantable spacer 1200 are numbered the same except preceded by the numeral '13', unless described otherwise herein. The implanted first spacer member 1304 of the surgically implantable spacer 1300 differs from the implanted first spacer member 1204 of the surgically implantable spacer 1200 in that the outer latch cantilevered arm hook 1264 is formed as a recession extending inward into a bottom surface of the spacer frame segment 1311. In an enhanced version, the implanted first spacer member 1304 would include a series of cantilevered hook receiving notch 1364 spatially arranged from the end proximate the inner latch cantilevered arm hook 1374. The series of cantilevered hook receiving notch 1364 introduces flexibility in the shape or radius of the arch of the implanted first spacer member 1304. The implanted first spacer member 1304 can include one or more arch retention features comprising an inner latch cantilevered arm hook 1374 located at a free end of the inner latch cantilevered arm 1370 and the respective cantilevered hook receiving notch 1364 or plurality of cantilevered hook receiving notch 1364. It is noted that this configuration can provide a thin and generally planar profile. In the exemplary surgically implantable spacer 1300, the implanted first spacer member 1304 is mated with an implanted second spacer member 1306 having coplanar surfaces.

Although not previously specified, each of the surgically implantable spacers 100, 500, 600, 800, 900, 1000, 1100, 1200, 1300 are preferably fabricated of a material having martensitic properties, such as nitinol. Alternatively, the surgically implantable spacers 100, 500, 600, 800, 900, 1000, 1100, 1200, 1300 can be fabricated of any suitable material. Each spacer segment or member would be fabricated of a contiguous section of material.

The various components of the surgically implantable spacers 100, 500, 600, 800, 900, 1000, 1100, 1200, 1300 can be fabricated from any suitable material. The components would be fabricated using any suitable metal working process or processes, including wire EDM, milling, polishing, laser cutting, water jet cutting, bending, forming, rolling, lathe, threading, and the like.

Although the primary application of the instant invention is directed towards an application as a spacer between adjoining bones, cartilage, and the like, it is understood that the concept of a preformed intermetallic compound can be used in other medical applications, wherein the shape changing effect can be employed to apply a tensile force between two ends thereof. The apparatus can be shaped to include a rolled end, wherein the apparatus can be cooled and straightened, affixed into the target location, then warmed, wherein the material returns to an undeformed shape, rolling or collecting the end sections or bowing the central portion, resulting in a shape that draws the ends together.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

REF NO. DESCRIPTION 100 surgically implantable spacer
102 spacer body
110 implanted spacer peripheral segment
111 spacer thickness
112 spacer control end
114 spacer insertion end
116 spacer side edge
118 spacer upper surface
119 spacer lower surface
120 segment defining slot
122 slot stress relief
124 implanted spacer inner segment
130 circumferential outer edge retention feature
140 inner segment retention feature
142 circumferential inner edge retention feature 150 threaded shaping passage
151 threaded shaping aperture orifice
152 blind receptacle
153 blind receptacle orifice
154 spacer control rod clearance slot
155 blind receptacle end wall
158 expansion force
160 threaded passage diameter
162 smooth passage diameter
164 slot thickness
200 spacer expansion control mechanism assembly
210 spacer shaping control rod
214 spacer control rod spanning segment
216 spacer control rod threaded segment
218 spacer control rod extension segment
220 spacer control sleeve
222 engaging end
230 spacer torsional control element
232 spacer torsional control section
234 spacer torsional control surface
299 insertion direction
300 first joint member
302 first vertebrae
304 first vertebrae first joint surface
306 first vertebrae second joint surface
310 second joint member
312 second vertebrae
314 second vertebrae second joint surface
316 second vertebrae second joint surface
320 intra-vertebral disc
322 intra-vertebral disc removal
400 replacement spacer insertion process flow diagram
402 obtain surgically implantable spacer step
404 cool surgically implantable spacer step
406 extend surgically implantable spacer into planar configuration step
408 insert surgically implantable spacer into joint step
410 remove extending force from surgically implantable spacer step
412 warm surgically implantable spacer step
414 surgically implantable spacer returns to preformed shape step
416 grafts embed within openings formed within the surgically implantable spacer step
500 surgically implantable spacer
504 implanted spacer central member
506 implanted spacer first peripheral member
508 implanted spacer second peripheral member
512 spacer control end
514 spacer insertion end
516 spacer side edge
518 spacer upper surface
519 spacer lower surface
522 stress relief formation
530 circumferential outer edge retention feature
540 inner member retention feature
542 circumferential inner edge retention feature
550 threaded shaping passage (threaded spacing element)
551 threaded shaping aperture orifice
552 blind receptacle
553 blind receptacle orifice
554 spacer control rod clearance slot
555 blind receptacle end wall
570 assembly pin (first component of pivot enabling element)
572 assembly pin receiving cavity (second component of pivot enabling element)
600 surgically implantable spacer
604 implanted spacer central member
606 implanted spacer first peripheral member
608 implanted spacer second peripheral member
616 spacer side edge
618 spacer upper surface
619 spacer lower surface
650 peripheral member compression retention through passage
651 threaded shaping aperture orifice
652 peripheral member compression retention blind receptacle (distal shaping element)
654 central member compression retention through passage
655 peripheral member compression retention blind receptacle end wall
670 assembly pin (first component of pivot enabling element)
672 assembly pin receiving cavity (second component of pivot enabling element)
678 spacer central member upper surface threading
679 spacer peripheral member lower surface threading
680 threaded spanner retention component (spanner retention element), (threaded spacing element)
682 threaded spanner retention component body
684 threaded spanner retention component distal end
686 spanner retention component threaded surface
688 threaded spanner retention component insertion driver receptacle
690 threaded spanner retention component interior cavity
692 grafting cavity
700 spacer compression retention mechanism assembly
710 spacer compression retention control rod
712 spacer compression retention control rod assembly bore
720 spacer compression retention mechanism assembly handle
722 spacer compression retention handle assembly bore
730 spacer compression retention assembly end component
740 spacer torsional control pin
800 surgically implantable spacer
804 implanted spacer central member
806 implanted spacer first peripheral member
808 implanted spacer second peripheral member
816 spacer side edge
818 spacer upper surface
819 spacer lower surface
820 spacer members interior edges
870 assembly pin (first component of pivot enabling element)
878 spacer central member spanner receiving slot
879 spacer peripheral member spanner receiving slot
880 planar spanning retention component (spanner retention element)
882 planar spanning retention component body
884 planar spanning retention component central receiving slot base supporting edge
885 planar spanning retention component central receiving slot side edge
886 planar spanning retention component outer receiving slot base supporting edge
887 planar spanning retention component outer receiving slot side edge
890 planer spanning retention component aperture
900 surgically implantable spacer
904 implanted spacer central member
906 implanted spacer first peripheral member
908 implanted spacer second peripheral member
912 spacer control end 914 spacer insertion end
916 spacer side edge
918 spacer upper surface
919 spacer lower surface
922 stress relief formation
930 circumferential outer edge retention feature
940 inner member retention feature
942 circumferential inner edge retention feature
950 threaded shaping passage (threaded spacing element)
951 threaded shaping aperture orifice
952 blind receptacle
953 blind receptacle orifice
954 spacer control rod clearance slot
955 blind receptacle end wall
970 assembly pin (first component of pivot enabling element)
972 assembly pin receiving cavity (second component of pivot enabling element)
974 pivotal spanner pivot pin
976 pivotal spanner pivot pin spacer receptacle
978 pivotal spanner component distal edge engagement feature
980 pivotal spanner component (spanner retention element)
982 pivotal spanner component distal edge
984 pivotal spanner pivot pin spanner receptacle
1000 surgically implantable spacer
1004 implanted spacer central member
1006 implanted spacer first peripheral member
1008 implanted spacer second peripheral member
1012 spacer control end
1014 spacer insertion end
1016 spacer side edge
1018 spacer upper surface
1019 spacer lower surface
1022 stress relief formation
1030 circumferential outer edge retention feature
1040 inner member retention feature
1042 circumferential inner edge retention feature
1050 pivotal threaded expansion shaping element
1051 expansion shaping element threading
1052 expansion shaping element blind receptacle (distal shaping element)
1054 spacer control rod clearance slot
1055 pivotal blind receptacle expansion shaping element
1056 bored expansion shaping element hinge pin receiving bore
1070 assembly pin (first component of pivot enabling element)
1071 segmented assembly pin
1072 assembly hinge pin receiving cavity (second component of pivot enabling element)
1073 assembly hinge pin receiving bore
1074 assembly hinge pin receiving slot
1077 pivotal shaping element clearance
1100 surgically implantable spacer
1104 implanted first spacer member
1106 implanted second spacer member
1110 spacer frame segment
1160 outer latch cantilevered arm
1162 outer latch cantilevered arm connectivity formation
1164 outer latch cantilevered arm hook
1165 outer latch cantilevered arm hook contact surface
1168 outer latch cantilevered arm length
1170 inner latch cantilevered arm
1172 inner latch cantilevered arm connectivity formation
1174 inner latch cantilevered arm hook
1175 inner latch cantilevered arm hook contact surface
1178 inner latch cantilevered arm length
1192 longitudinal mirror plane
1194 lateral mirror plane
1199 recessed formation
1200 surgically implantable spacer
1204 implanted first spacer member
1206 implanted second spacer member
1210 spacer frame latching segment
1211 spacer frame segment
1230 circumferential outer edge retention feature
1240 first spacer member retention feature
1260 outer latch cantilevered arm
1262 outer latch cantilevered arm connectivity formation
1264 outer latch cantilevered arm hook
1265 outer latch cantilevered arm hook contact surface
1268 outer latch cantilevered arm length
1270 inner latch cantilevered arm
1272 inner latch cantilevered arm connectivity formation
1274 inner latch cantilevered arm hook
1275 inner latch cantilevered arm hook contact surface
1278 inner latch cantilevered arm length
1279 recessed formation
1300 surgically implantable spacer
1304 implanted first spacer member
1306 implanted second spacer member
1310 spacer frame latching segment
1311 spacer frame segment
1330 circumferential outer edge retention feature
1340 first spacer member retention feature
1360 outer latch cantilevered arm
1362 outer latch cantilevered arm connectivity formation
1364 cantilevered hook receiving notch
1365 outer latch cantilevered arm hook contact surface
1368 outer latch cantilevered arm length
1370 inner latch cantilevered arm
1372 inner latch cantilevered arm connectivity formation
1374 inner latch cantilevered arm hook
1375 inner latch cantilevered arm hook contact surface
1378 inner latch cantilevered arm length
1379 recessed formation

What is claimed is:

1. A surgically implantable spacer comprising:

a central spacer member, said central spacer member having an elongated central spacer member body bound by a central spacer member peripheral edge comprising a central spacer member insertion end located at a first elongated end and a central spacer member controller end located at a second, opposite elongated end, and a pair of elongated assembly sidewalls, each a pair of elongated sidewall extending between said first elongated end and said second elongated end;

a pair of peripheral spacer members, each peripheral spacer member having an elongated peripheral spacer member body bound by a peripheral spacer member peripheral edge comprising a peripheral spacer member insertion end located at a first peripheral spacer member elongated end and a peripheral spacer member controller end located at a second, opposite peripheral spacer member elongated end, an exposed elongated peripheral spacer member assembly sidewall and an assembly elongated peripheral spacer member assembly sidewall, each of said exposed elongated peripheral spacer member sidewall and said assembly elongated peripheral spacer member assembly sidewall extending between said first peripheral spacer member elongated end and said second peripheral spacer member elongated end;

a spacer control rod clearance slot formed within said central spacer member, said spacer control rod clearance slot extending along a longitudinal centerline of said central spacer member;

a threaded shaping element located proximate said central spacer member controller end, said threaded shaping element comprising a threaded bore oriented parallel to and in linear alignment with said spacer member longitudinal centerline;

a distal shaping element located proximate said central spacer member insertion end, said distal shaping element comprising a blind receptacle oriented parallel to a spacer member longitudinal centerline and in linear alignment with said threaded bore and said spacer member longitudinal centerline; and at least two assembly hinge formations;

wherein said central spacer member is located between each of said peripheral spacer members, oriented having each said elongated assembly sidewall facing a mating said assembly elongated peripheral spacer member assembly sidewall, said central spacer member and said peripheral spacer members are oriented having like elongated ends proximate one another, wherein each of said at least two pivot enabling elements pivotally assemble said elongated assembly sidewall and said mating said assembly elongated peripheral spacer member assembly sidewall to one another at a location near each said elongated end;

wherein said central spacer member is shaped into an un-deformed configuration having each implanted spacer peripheral segment forming an arch in a first direction and said implanted spacer central segment forming an arch in a second direction, wherein said first direction is opposite of said second direction, wherein said surgically implantable spacer is temporarily shaped for insertion, wherein each implanted spacer peripheral segment and said implanted spacer central segment are deformed into a planar configuration by engaging a spacer shaping control rod with said threaded bore and said blind receptacle.

2. A surgically implantable spacer as recited in claim 1, said central spacer member and said pair of peripheral spacer members being formed of a material having martensitic properties.

3. A surgically implantable spacer as recited in claim 1, said central spacer member and said pair of peripheral spacer members being formed of a material having martensitic properties wherein said material is nitinol.

4. A surgically implantable spacer as recited in claim 1, wherein said threaded shaping element and said distal shaping element are pivotally assembled to said surgically implantable spacer.

5. A surgically implantable spacer as recited in claim 1, wherein said blind receptacle further comprises a threaded surface.

6. A surgically implantable spacer as recited in claim 1, further comprising at least one placement retention feature formed on at least one of said central spacer member and said peripheral spacer member.

7. A surgically implantable spacer as recited in claim 1, further comprising a spanner retention element, said spanner retention element adapted to maintain a span between opposite facing surfaces of said central spacer member and each of said pair of peripheral spacer members when said surgically implantable spacer into said un-deformed, spanned configuration.

8. A surgically implantable spacer as recited in claim 1, further comprising a spanner retention element, said spanner retention element adapted to maintain a span between opposite facing surfaces of said central spacer member and each of said pair of peripheral spacer members when said surgically implantable spacer into said un-deformed, spanned configuration, said spanner retention element being at least one of:

a planar spanner retention element, a planar spanner retention element comprising at least one of: (a) a central spanner element receiving notch extending inward from a first edge of said planar spanner retention element and a peripheral spanner element receiving notch extending inward from a second, opposite edge of said planar spanner retention element, a pivotal spanner retention element, a pivotal spanner retention element adapted to engage with a pivotal spanner component distal edge engagement feature formed within a respective mating spacer member surface, a threaded spanner retention element, at least one cantilevered hook formed within a concave formed surface of at least one of said central spacer member and said peripheral spacer member, said at least one cantilevered hook adapted to engage with a mating hook engaging feature formed within said concave formed surface of said same at least one of said central spacer member and said peripheral spacer member, at least one cantilevered hook formed within a concave formed surface of at least one of said central spacer member and said peripheral spacer member, said at least one cantilevered hook adapted to engage with one of a series of a mating hook engaging features spatially formed within said concave formed surface of said same at least one of said central spacer member and said peripheral spacer member, at least one cantilevered hook formed within a concave formed surface of at least one of said central spacer member and said peripheral spacer member, said at least one cantilevered hook adapted to engage with a mating hook formed within said concave formed surface of said same at least one of said central spacer member and said peripheral spacer member, and at least one cantilevered hook formed within a concave formed surface of at least one of said central spacer member and said peripheral spacer member, said at least one cantilevered hook adapted to engage with a mating cantilevered hook formed within said concave formed surface of said same at least one of said central spacer member and said peripheral spacer member.

9. A surgically implantable spacer comprising:

a central spacer member, said central spacer member having an elongated central spacer member body bound by a central spacer member peripheral edge comprising a central spacer member insertion end located at a first elongated end and a central spacer member controller end located at a second, opposite elongated end, and a pair of elongated assembly sidewalls, each a pair of elongated sidewall extending between said first elongated end and said second elongated end;

a pair of peripheral spacer members, each peripheral spacer member having an elongated peripheral spacer member body bound by a peripheral spacer member peripheral edge comprising a peripheral spacer member insertion end located at a first peripheral spacer member elongated end and a peripheral spacer member controller end located at a second, opposite peripheral spacer member elongated end, an exposed elongated peripheral spacer member assembly sidewall and an assembly elongated peripheral spacer member assembly sidewall, each of said exposed elongated peripheral spacer member sidewall and said assembly elongated peripheral spacer member assembly sidewall extending between said first peripheral spacer member elongated end and said second peripheral spacer member elongated end; and
a first spacer span control feature and a second spacer control feature;
wherein said central spacer member is located between each of said peripheral spacer members, oriented having each said elongated assembly sidewall facing a mating said assembly elongated peripheral spacer member assembly sidewall, said central spacer member and said peripheral spacer members are oriented having like elongated ends proximate one another,
wherein each of said at least two pivot enabling elements pivotally assemble said elongated assembly sidewall and said mating said assembly elongated peripheral spacer member assembly sidewall to one another at a location near each said elongated end;
wherein said central spacer member is shaped into an un-deformed configuration having each implanted spacer peripheral segment forming an arch in a first direction and said implanted spacer central segment forming an arch in a second direction, wherein said first direction is opposite of said second direction,
wherein said surgically implantable spacer is temporarily shaped for insertion, wherein each implanted spacer peripheral segment and said implanted spacer central segment are deformed into a planar configuration by engaging a spacer shaping control rod with said first spacer span control feature and said second spacer control feature.

10. A surgically implantable spacer as recited in claim 9, said central spacer member and said pair of peripheral spacer members being formed of a material having martensitic properties.

11. A surgically implantable spacer as recited in claim 9, said central spacer member and said pair of peripheral spacer members being formed of a material having martensitic properties wherein said material is nitinol.

12. A surgically implantable spacer as recited in claim 9, wherein said first spacer span control feature is provided as a first bore extending generally centrally through said central shaping member parallel to a transverse axis thereof and said second spacer span control feature is provided as a pair of second bores, each second bore extending through each of said pair of peripheral shaping members, wherein said first bore and each of said second bores are arranged in a linear alignment with one another,
wherein said surgically implantable spacer is retained within said temporary shape for insertion by inserting a spacer compression retention control rod through each of said first bore and said second bores.

13. A surgically implantable spacer as recited in claim 9, wherein said first spacer span control feature is a threaded shaping element and said second spacer span control feature is a distal shaping element, wherein said threaded shaping element and said distal shaping element are pivotally assembled to said surgically implantable spacer.

14. A surgically implantable spacer as recited in claim 9, wherein said first spacer span control feature is a first threaded shaping element and said second spacer span control feature is a second threaded shaping element, wherein said threaded shaping element and said distal shaping element are pivotally assembled to said surgically implantable spacer, wherein said first threaded shaping element contains threads in a first threaded direction and said second threaded shaping element contains threads in a second, opposite threaded direction.

15. A surgically implantable spacer as recited in claim 9, further comprising a spanner retention element, said spanner retention element adapted to maintain a span between opposite facing surfaces of said central spacer member and each of said pair of peripheral spacer members when said surgically implantable spacer into said un-deformed, spanned configuration.

16. A surgically implantable spacer as recited in claim 9, further comprising a spanner retention element, said spanner retention element adapted to maintain a span between opposite facing surfaces of said central spacer member and each of said pair of peripheral spacer members when said surgically implantable spacer into said un-deformed, spanned configuration, said spanner retention element being at least one of:
a planar spanner retention element,
a planar spanner retention element comprising at least one of: (a) a central spanner element receiving notch extending inward from a first edge of said planar spanner retention element and a peripheral spanner element receiving notch extending inward from a second, opposite edge of said planar spanner retention element,
a pivotal spanner retention element,
a pivotal spanner retention element adapted to engage with a pivotal spanner component distal edge engagement feature formed within a respective mating spacer member surface,
a threaded spanner retention element,
at least one cantilevered hook formed within a concave formed surface of at least one of said central spacer member and said peripheral spacer member, said at least one cantilevered hook adapted to engage with a mating hook engaging feature formed within said concave formed surface of said same at least one of said central spacer member and said peripheral spacer member,
at least one cantilevered hook formed within a concave formed surface of at least one of said central spacer member and said peripheral spacer member, said at least one cantilevered hook adapted to engage with one of a series of a mating hook engaging features spatially formed within said concave formed surface of said same at least one of said central spacer member and said peripheral spacer member,
at least one cantilevered hook formed within a concave formed surface of at least one of said central spacer member and said peripheral spacer member, said at least one cantilevered hook adapted to engage with a mating hook formed within said concave formed surface of said same at least one of said central spacer member and said peripheral spacer member, and
at least one cantilevered hook formed within a concave formed surface of at least one of said central spacer member and said peripheral spacer member, said at least one cantilevered hook adapted to engage with a mating cantilevered hook formed within said concave formed surface of said same at least one of said central spacer member and said peripheral spacer member.

17. A surgically implantable spacer as recited in claim 9, further comprising at least one placement retention feature formed on at least one of said central spacer member and said peripheral spacer member.

18. A surgically implantable spacer comprising:
- a first spacer member, said first spacer member having an arched elongated first spacer member body defining a convex outer surface and a concave inner surface, said convex outer surface and said concave inner surface having a first spacer member peripheral edge extending therebetween, said first spacer member peripheral edge comprising a pair of spacer member end walls, each spacer member end wall being located at a respective elongated end of said first spacer member and a pair of elongated sidewalls, each a pair of elongated sidewall extending between like edges of each said spacer member end wall, said first spacer member being contiguous and formed of a material having martensitic properties;
- a second spacer member, said second spacer member having an arched elongated second spacer member body defining a convex outer surface and a concave inner surface, said convex outer surface and said concave inner surface having a second spacer member peripheral edge extending therebetween, said second spacer member peripheral edge comprising a pair of spacer member end walls, each spacer member end wall being located at a respective elongated end of said second spacer member and a pair of elongated sidewalls, each a pair of elongated sidewall extending between like edges of each said spacer member end wall, said second spacer member being contiguous and formed of a material having martensitic properties;
- said first spacer member and said second spacer member being pivotally assembled to one another at each elongated end, said first spacer member and said second spacer member being oriented having convex surfaces facing one another;
- a first spacer span control feature and a second spacer control feature;
- wherein said first spacer member is located between each of said peripheral spacer members, oriented having each said elongated assembly sidewall facing a mating said assembly elongated peripheral spacer member assembly sidewall, said first spacer member and said peripheral spacer members are oriented having like elongated ends proximate one another,
- wherein, in an un-deformed configuration, said surgically implantable spacer having a centered region of said first arch shaped spacer member and a like centered region of said second arch shaped spacer member extended away from one another,
- wherein, in a deformed configuration, said surgically implantable spacer having a centered region of said first arch shaped spacer member and a like centered region of said second arch shaped spacer member drawn towards one another, deforming each of said first arch shaped spacer member and said second arch shaped spacer member into a substantially planar shape.

19. A surgically implantable spacer as recited in claim 18, further comprising at least two pivot enabling elements,
- wherein each of said at least two pivot enabling elements pivotally assemble said first arch shaped spacer member and said second arch shaped spacer member to one another at a location near each said elongated end.

20. A surgically implantable spacer as recited in claim 18, further comprising at least one placement retention feature formed on at least one of said central spacer member and said peripheral spacer member.

21. A surgically implantable spacer as recited in claim 18, further comprising a spanner retention element, said spanner retention element adapted to maintain a span between opposite facing surfaces of said central spacer member and each of said pair of peripheral spacer members when said surgically implantable spacer into said un-deformed, spanned configuration.

* * * * *